US006277878B1

(12) United States Patent
Nakao et al.

(10) Patent No.: US 6,277,878 B1
(45) Date of Patent: Aug. 21, 2001

(54) SUBSTITUTED INDOLE COMPOUNDS AS ANTI-INFLAMMATORY AND ANALGESIC AGENTS

(75) Inventors: Kazunari Nakao; Rodney W. Stevens; Kiyoshi Kawamura; Chikara Uchida, all of Chita-gun (JP)

(73) Assignee: Pfizer Inc, New York, NY (US)

( * ) Notice: Subject to any disclaimer, the term of this patent is extended or adjusted under 35 U.S.C. 154(b) by 0 days.

(21) Appl. No.: 09/383,353

(22) Filed: Aug. 26, 1999

(30) Foreign Application Priority Data

Sep. 7, 1998 (WO) .................................. PCT/IB98/01382

(51) Int. Cl.[7] .................. A61K 31/404; A61K 31/5355; C07D 209/04
(52) U.S. Cl. ................. 514/419; 514/233.2; 514/254.09; 514/422; 514/423; 544/143; 544/144; 544/373; 546/278.1; 548/465; 548/483
(58) Field of Search ................. 514/419, 422, 514/423, 254.09, 233.2; 544/143, 144, 373; 546/278.1; 548/465, 483

(56) References Cited

U.S. PATENT DOCUMENTS 5,145,845 * 9/1992 Johnson et al. ................. 514/80
5,189,054 * 2/1993 Salituro et al. ................. 514/419

OTHER PUBLICATIONS

Prasit et al., Selective Cycoloxygenase–2 Inhibitors. Ann. Rev. Med. Chem. 32, 211, (1997).*
Fenwick, et al., GUT, vol. 26 (Suppl 11), A44 (2000).
Mann, et al., Gastroenterology, vol. 118(4 Suppl 2 Pt 1), p 177 (2000).
Payne, R. J., Pain, vol. 1(3 Suppl), pp. 14–18 (2000).
O'Banion, et al., Crit. Rev. Neurobiol., vol. 13(1), pp. 45–82 (1999).
Trimboli, et al., Cancer Research, vol. 59(24), pp. 6171–6177 (1999); and.
Two IMSWorld Publications, R&D Focus, Product Names Celebrex and Vioxx.

* cited by examiner

Primary Examiner—Richard L. Raymond
Assistant Examiner—Hong Liu
(74) Attorney, Agent, or Firm—Peter C. Richardson; Paul H. Ginsburg; Elsa Djuardi

(57) ABSTRACT

This invention provides a compound of the following formula:

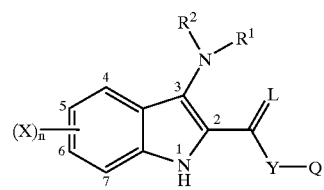

(I)

or the pharmaceutically acceptable salts thereof wherein $R^1$ is H or $C_{1-4}$ alkyl; $R^2$ is $C(=L')R^3$ or $So_2R^4$; Y is a direct bond or $C_{1-4}$ alkylene; L and L' are independently oxygen or sulfur; Q is selected from the following: $C_{1-6}$ alkyl, halo-substituted $C_{1-4}$ alkyl, optionally substituted $C_{3-7}$ cycloalkyl, optionally substituted phenyl or naphthyl, optionally substituted 5 or 6-membered monocyclic aromatic group;
$R^3$ is $-OR^6$, $-NR^7R^8$, $N(OR^1)R^7$ or a group of formula:

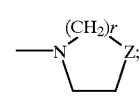

Z is a direct bond, O, S or $NR^5$; $R^4$ is $C_{1-6}$ alkyl, halo-substituted $C_{1-4}$ alkyl, optionally substituted phenyl or naphthyl; $R^5$ is $C_{1-4}$ alkyl or halo-substituted $C_{1-4}$ alkyl; $R^6$ is $C_{1-4}$ alkyl $C_{3-7}$ cycloalkyl, $C_{1-4}$ alkyl-$C_{3-7}$ cycloalkyl, halo-substituted $C_{1-4}$ alkyl, optionally substituted $C_{1-4}$ alkyl-phenyl or phenyl; $R^7$ and $R^8$ are each selected from the following: H, optionally substituted $C_{1-6}$ alkyl, optionally substituted $C_{3-7}$ cycloalkyl, optionally substituted $C_{1-4}$ alkyl-$C_{3-7}$ cycloalkyl, and optionally substituted $C_{1-4}$ alkyl-phenyl or phenyl; X is each selected from halo, $C_{1-4}$ alkyl, halo-substituted $C_{1-4}$ alkyl, OH, $C_{1-4}$ alkoxy, halo-substituted $C_{1-4}$ alkoxy, $C_{1-4}$ alkylthio, $NO_2$, $NH_2$, di-($C_{1-4}$ alkyl)amino and CN; n is 0, 1, 2 or 3; and r is 1, 2 or 3. This invention also provides a pharmaceutical composition useful for the treatment of a medical condition in which prostaglandins are implicated as pathogens.

11 Claims, No Drawings

SUBSTITUTED INDOLE COMPOUNDS AS ANTI-INFLAMMATORY AND ANALGESIC AGENTS

TECHNICAL FIELD

This invention relates to novel substituted indoles as pharmaceutical agents. This invention specifically relates to compounds, compositions and methods for the treatment or alleviation of pain and inflammation and other inflammation-associated disorders, such as arthritis.

BACKGROUND ART

Nonsteroidal antiinflammatory drugs (NSAIDs) are widely used in treating pain and the signs and symptoms of arthritis because of their analgesic and anti-inflammatory activity. It is accepted that common NSAIDs work by blocking the activity of cyclooxygenase (COX), also known as prostaglandin G/H synthase (PGHS), the enzyme that converts arachidonic acid into prostanoids. Prostaglandins, especially prostaglandin $E_2$ ($PGE_2$), which is the predominant eicosanoid detected in inflammation conditions, are mediators of pain, fever and other symptoms associated with inflammation. Inhibition of the biosynthesis of prostaglandins has been a therapeutic target of anti-inflammatory drug discovery. The therapeutic use of conventional NSAIDs is, however, limited due to drug associated side effects, including life threatening ulceration and renal toxicity An alternative to NSAIDs is the use of corticosteriods, however, long term therapy can also result in severe side effects.

Recently, two forms of COX were identified, a constitutive isoform (COX-1) and an inducible isoform (COX-2) of which expression is upregulated at sites of inflammation (Vane, J. R.; Mitchell, J. A.; Appleton, I.; Tomlinson, A.; Bishop-Bailey, D.; Croxtoll, J.;Willoughby, D. A. Proc. Natl. Acad. Sci. USA, 1994, 91, 2046). COX-1 is thought to play a physiological role and to be responsible for gastrointestinal and renal protection. On the other hand, COX-2 appears to play a pathological role and to be the predominant isoform present in inflammation conditions. A pathological role for prostaglandins has been implicated in a number of human disease states including rheumatoid and osteoarthritis, pyrexia, asthma, bone resorption, cardiovascular diseases, nephrotoxicity, atherosclerosis, hypotension, shock, pain, cancer, and Alzheimer disease. The NSAIDs currently on market inhibit both isoforms of COX with little variation for selectivity, explaining their beneficial (inhibition of COX-2) and deleterious effects (inhibition of COX-1). It is believed that compounds that would selectively inhibit the biosynthesis of prostaglandins by intervention of the induction phase of the inducible enzyme cyclooxygenase-2 and/or by intervention of the activity of the enzyme cyclooxygenase-2 on arachidonic acid would provide alternate therapy to the use of NSAIDs or corticosteriods in that such compounds would exert anti-inflammatory effects without the adverse side effects associated with COX-1 inhibition.

Heterocyclylcarbonyl substituted benzofuranyl-ureas are disclosed in European patent publication number EP 0 779 291 A1.

A variety of indole compounds are known and are disclosed in several patent applications. The International Publication Numbers WO 96/37467, WO 96/37469, UK Patent Publication GB 2283745 A and US Publication Number 5510368 disclose 2-methyl-N-substituted indole compounds as cyclooxygenase-2 Inhibitors.

BRIEF DISCLOSURE OF THE INVENTION

The present invention provides a compound of the following formula:

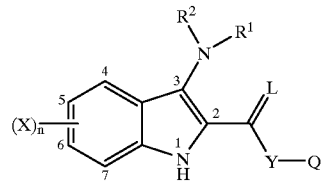

(I)

or the pharmaceutically acceptable salts thereof wherein
$R^1$ is hydrogen or $C_{1-4}$ alkyl; $R^2$ is $C(=L')R^3$ or $SO_2R^4$; Y is a direct bond or $C_{1-4}$ alkylene; L and L' are independently oxygen or sulfur;
Q is selected from the following:
(Q-a) $C_{1-6}$ alkyl,
(Q-b) halo-substituted $C_{1-4}$ alkyl,
(Q-c) $C_{3-7}$ cycloalkyl optionally substituted with one or two substituents independently selected from $C_{1-4}$ alkyl, halo-substituted $C_{1-4}$ alkyl, $C_{1-4}$ alkoxy, hydroxy and halo,
(Q-d) phenyl or naphthyl, the phenyl and naphthyl being optionally substituted with one, two or three substituents independently selected from halo, $C_{1-4}$ alkyl, halo-substituted $C_{1-4}$, alkyl, hydroxy, $C_{1-4}$ alkoxy, nitro, halo-substituted $C_{1-4}$ alkoxy, $S(O)_mR^5$, $SO_2NH_2$, $SO_2N(C_{1-4}$ alkyl$)_2$, amino, $C_{1-4}$ alkylamino, di-($C_{1-4}$ alkyl)amino, $NR^1C(O)R^5$, CN, $C_{1-4}$ alkyl-OH and $C_{1-4}$ alkyl-$OR^5$,
(Q-e) a 5-membered monocyclic aromatic group containing one heteroatom selected from O, S and N and optionally containing one, two or three nitrogen atom(s) in addition to said heteroatom, and said monocyclic armomatic group being optionally substituted with one, two or three substituents independently selected from halo, $C_{1-4}$ alkyl, halo-substituted $C_{1-4}$ alkyl, hydroxy, $C_{1-4}$ alkoxy, halo-substituted $C_{1-4}$ alkoxy, amino, $C_{1-4}$ alkylamino, di-($C_{1-4}$ alkyl)amino, $C_{1-4}$ alkyl-OH and $C_{1-4}$ , alkyl-$OR^5$, and
(Q-f) a 6-membered monocyclic aromatic group containing one nitrogen atom and optionally containing one, two or three additional nitrogen atom(s), and said monocyclic armomatic group being optionally substituted with one, two or three substituents independently selected from halo, $C_{1-4}$ alkyl, halo-substituted $C_{1-4}$ alkyl, hydroxy, $C_{1-4}$ alkoxy, halo-substituted $C_{1-4}$ alkoxy, amino, $C_{1-4}$ alkylamino, di-($C_{1-4}$ alkyl)amino, $C_{1-4}$ alkyl-OH and $C_{1-4}$ alkyl-$OR^5$;
$R^3$ is —$OR^6$, —$NR^7R^8$, $N(OR^1)R^7$ or a group of formula:

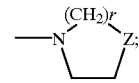

Z is a direct bond, oxygen, sulfur or $NR^5$;
$R^4$ is $C_{1-6}$, alkyl, halo-substituted $C_{1-4}$ alkyl, $C_{1-4}$ alkyl-OH, —$NR^7R^8$, phenyl or naphthyl, the phenyl and naphthyl being optionally substituted with one, two or three substituents independently selected from halo, $C_{1-4}$ alkyl, halo-substituted $C_{1-4}$ alkyl, hydroxy, $C_{1-4}$ alkoxy and halo-substituted $C_{1-4}$ , alkoxy;
$R^5$ is $C_{1-4}$ , alkyl or halo-substituted $C_{1-4}$ alkyl;
$R^6$ is $C_{1-4}$ alkyl, $C_{3-7}$ , cycloalkyl, $C_{1-4}$ alkyl-$C_{3-7}$ cycloalkyl, halo-substituted $C_{1-4}$ alkyl, $C_{1-4}$ alkyl-phenyl or phenyl, the phenyl moiety being optionally substituted with one, or two substituents independently selected from halo, $C_{1-4}$ alkyl, halo-substituted $C_{1-4}$ alkyl, hydroxy, $C_{1-4}$ alkoxy, $C_{1-4}$ alkylthio, amino, di-($C_{1-4}$ alkyl)amino and nitro;

$R^7$ and $R^8$ are independently selected from the following:
(a) hydrogen,
(b) $C_{1-6}$ alkyl optionally substituted with a substituent independently selected from halo, hydroxy, $C_{1-4}$ alkoxy, amino, $C_{1-4}$ alkylamino and di-($C_{1-4}$ alkyl) amino,
(c) $C_{3-7}$ cycloalkyl optionally substituted with a substituent independently selected from hydroxy, $C_{1-4}$ alkyl and $C_{1-4}$ alkoxy,
(d) $C_{1-4}$ alkyl-$C_{3-7}$ cycloalkyl optionally substituted with a substituent independently selected from hydroxy, $C_{1-4}$ and $C_{1-4}$ alkoxy, and
(f) $C_{1-4}$ alkyl-phenyl or phenyl, the phenyl moiety being optionally substituted with one or two substituents independently selected from halo, $C_{1-4}$ alkyl, halo-substituted $C_{1-4}$ alkyl, hydroxy, $C_{1-4}$ alkoxy, $C_{1-4}$ alkylthio, nitro, amino, di-($C_{1-4}$ alkyl)amino and CN;

X is independently selected from halo, $C_{1-4}$ alkyl, halo-substituted $C_{1-4}$ alkyl, hydroxy, $C_{1-4}$ alkoxy, halo-substituted $C_{1-4}$ alkoxy, $C_{1-4}$ alkylthio, nitro, amino, di-($C_{1-4}$ alkyl) amino and CN;

m is 0, 1 or 2; n is 0, 1, 2 or 3; and r is 1, 2 or 3.

The indole compounds of the present invention exhibit inhibition of COX activity. Preferably compounds of this invention exhibit inhibitory activity against COX-2, with more preferable compounds having COX-2 selectivity.

Accordingly, the present invention also provides a pharmaceutical composition, useful for the treatment of a medical condition in which prostaglandins are implicated as pathogens, which comprises a compound of the formula (I) and the pharmaceutically acceptable salts thereof.

Further, the present invention provides a method for the treatment of a medical condition in which prostaglandins are implicated as pathogens, in a mammalian subject, which comprises administering to said subject a therapeutically effective amount of said pharmaceutical composition.

The medical conditions in which prostaglandins are implicated as pathogens, include the relief of pain, fever and inflammation of a variety of conditions including rheumatic fever, symptoms associated with influenza or other viral infections, common cold, low back and neck pain, dysmenorrhea, headache, toothache, sprains and strains, myositis, neuralgia, synovitis, arthritis including rheumatoid arthritis, degenerative joint disease (osteoarthritis), gout, ankylosing spondylitis, systemic lumpus erythematosus and juvenile arthritis, bursitis, bums, injuries following surgical and dental procedures.

The compounds and pharmaceutical composition of this invention may inhibit cellular neoplastic transformations and metastatic tumor growth and thus may be used in the treatment and/or prevention of cancers in the colon, breast, skin, esophagus, stomach, urinary bladder, lung and liver. The compounds and pharmaceutical composition of this invention were used in the treatment and/or prevention of cyclooxygenase-mediated proliferation disorders such as which occur in diabetic retinopathy and tumor angiogenesis.

The compounds and pharmaceutical composition of this invention may inhibit prostaniod-induced smooth muscle contraction by preventing the synthesis of contractile prostanoids, and thus may be of use in the treatment of dysmenorrhea, premature labor, asthma and eosinophil related disorders and in the treatment of neurodegenerative diseases such as Alzheimer's and Parkinson's disease, and for the treatment of bone loss (treatment of osteoarritis), stroke, seizures, migraine, multiple sclevosis, AIDS and encephaloathy.

By virtue of the COX-2 activity and/or specificity for COX-2 over COX-1, such compounds will prove useful as an alternative to conventional NSAIDs particularly where such NSAIDs may be contra-indicated such as in patients with ulcers (such as peptic ulcers and gastric ulcers), gastritis, regional enterotis, ulcerative colitis, diverticulitis or with a recurrent history of GI lesions, GI bleeding, coagulation disorders including anemia such as hypoprothrombinemia, haemophilia and other bleeding problems; kidney disease; prior to surgery of taking of anticoagulants.

DETAILED DISCLOSURE OF THE INVENTION

As used herein, "halo" is fluoro, chloro, bromo or iodo.

As used herein, the term "$C_{1-4}$ alkyl" means straight or branched chain saturated radicals of 1 to 4 carbon atoms, including, but not limited to methyl, ethyl, n-propyl, isopropyl, n-butyl, isobutyl, sec-butyl, tert-butyl, and the like.

As used herein, an example of "halo-substituted alkoxy" is chloromethoxy, dichloromethoxy, fluoromethoxy, difluoromethoxy, trifluoromethoxy, 2,2,2-trichloroethoxy, and the like.

As used herein, an example of "alkoxy" is methoxy, ethoxy, n-propoxy, isopropoxy, n-butoxy, isobutoxy, sec-butoxy, tert-butoxy, and the like.

As used herein, an example of "alkylthio" is methylthio, ethylthio, n-propylthio, isopropylthio, n-butylthio, isobutylthio, sec-butylthio, tert-butylthio, and the like.

As used herein, an example of di-($C_{1-4}$ alkyl)amino is dimethylamino, diethylamino, dipropylamino, N-methyl-N-ethylamino, N-methyl-N-propylamino, N-methyl-N-butylamino, N-ethyl-N-propylamino, and the like.

As used herein, an example of $C_{1-4}$ alkylamino is methylamino, ethylamino, n-propylamino, isopropylamino, n-butylamino, isobutylamino, sec-butylamino, tert-butylamino, and the like.

As used herein, an example of HO-($C_{1-4}$)alkyl is hydroxymethyl, hydroxyethyl (e.g., 1-hydroxyethyl and 2-hydroxyethyl), hydroxypropyl (e.g., 1-hydroxypropyl, 2-hydroxypropyl and 3-hydroxypropyl), and the like.

As used herein, an example of $C_{1-4}$ alkyl-$OR^5$ is methoxymethyl, methoxyethyl (e.g., 1- methoxyethyl and 2-methoxyethyl), methoxypropyl (e.g., 1-methoxypropyl, 2-methoxypropyl and 3-methoxypropyl), ethoxymethlyl, ethoxypropyl, and the like.

As used herein, an example of $C_{1-4}$ alkylene is methylene, ethylene, trimethylene or tetramethylene, and the like.

As used herein, an example of $C_{1-4}$ alkoxy-$C_{1-4}$ alkyl is methoxymethyl, methoxyethyl, methoxypropyl, methoxybutyl, ethoxymethyl, ethoxyethyl, ethoxypropyl, and the like.

As used herein, the term "halo-substituted alkyl" refers to an alkyl radical as described above substituted with one or more halos included, but not limited to, chloromethyl, dichloromethyl, fluoromethyl, difluoromethyl, trifluoromethyl, 2,2,2-trichloroethyl, and the like.

As used herein, the term "$C_{3-7}$ cycloalkyl" means carbocyclic radicals, of 3 to 7 carbon atoms, including, but not limited to cyclopropyl, cyclobutyl, cyclopentyl, cyclohexyl, cycloheptyl, and the like.

As used herein, a 5-membered monocyclic aromatic group usually has one heteroatom selected from O, S and N in the ring. In addition to said heteroatom, the monocyclic aromatic group may optionally have up to three N atoms in the ring. For example, the 5-membered monocyclic group includes thienyl, furyl, thiazolyl (e.g., 1,3-thiazolyl, 1,2-thiazolyl), imidazolyl, pyrrolyl, oxazolyl (e.g., 1,3-oxazolyl, 1,2-oxazolyl), pyrazolyl, tetraolyl, triazolyl (e.g., 1,2,3-triazolyl, 1,2,4-triazolyl), oxadiazolyl (e.g., 1,2,3-oxadiazolyl), thiadiazolyl (e.g., 1,3,4-thiadiazolyl) and the like.

As used herein, an example of a 6-membered monocyclic aromatic group includes pyridyl, pyrazinyl, pyrimidinyl, pyridazinyl, triazinyl (e.g., 1,3,5-triazinyl), tetrazinyl and the like.

Preferred compounds of this invention are those of the formula (I) wherein $R^1$ is hydrogen, methyl, ethyl, propyl or butyl; $R^2$ is C(=L')$R^3$ or SO$_2$$R^4$; Y is a direct bond, methylene, ethylene, trimethylene or tetramethylene; L and L' are oxygen; Q is selected from the following:

(Q-c) $C_{3-7}$ cycloalkyl optionally substituted with one or two substituents independently selected from $C_{1-4}$ alkyl, halo-substituted $C_{1-4}$ alkyl, $C_{1-4}$ alkoxy, hydroxy and halo, (Q-d) phenyl or naphthyl, the phenyl and naphthyl being optionally substituted with one, two or three substituents independently selected from halo, $C_{1-4}$ alkyl, halo-substituted $C_{1-4}$ alkyl, hydroxy, $C_{1-4}$ alkoxy, nitro, halo-substituted $C_{1-4}$ alkoxy, S(O)$_m$$R^5$, SO$_2$NH$_2$, SO$_2$N($C_{1-4}$ alkyl)$_2$, amino, $C_{1-4}$ alkylamino, di-($C_{1-4}$ alkyl)amino, NR$^1$C(O)$R^5$, CN, $C_{1-4}$ alkyl-OH and $C_{1-4}$ alkyl-OR$^5$, (Q-e) a 5-membered monocyclic aromatic group selected from thienyl, furyl, thiazolyl, imidazolyl, pyrrolyl, oxazolyl, pyrazolyl, tetrazolyl, triazolyl, oxadiazolyl and thiadiazolyl, and said monocyclic armomatic group being optionally substituted with one, two or three substituents independently selected from halo, $C_{1-4}$ alkyl, halo-substituted $C_{1-4}$ alkyl, hydroxy, $C_{1-4}$ alkoxy, halo-substituted $C_{1-4}$ alkoxy, amino, $C_{1-4}$ alkylamino, di-($C_{1-4}$ alkyl)amino, $C_{1-4}$ alkyl-OH and $C_{1-4}$ alkyl-OR$^5$, and (Q-f) a 6-membered monocyclic aromatic group selected from pyridyl, pyrazinyl, pyrimidinyl, pyridazinyl, triazinyl and tetrazinyl, and said monocyclic armomatic group being optionally substituted with one, two or three substituents independently selected from halo, $C_{1-4}$ alkyl, halo-substituted $C_{1-4}$ alkyl, hydroxy, $C_{1-4}$ alkoxy, halo-substituted $C_{1-4}$ alkoxy, amino, $C_{1-4}$ alkylamino, di-($C_{1-4}$ alkyl)amino, $C_{1-4}$ alkyl-OH and $C_{1-4}$ alkyl-OR$^5$;

$R^3$ is —OR$^6$, —NR$^7$R$^8$, N(OR$^1$)R$^7$ or a group of formula:

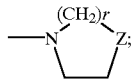

Z is a direct bond, oxygen or NR$^5$;

$R^4$ is $C_{1-6}$ alkyl, halo-substituted $C_{1-4}$ alkyl, $C_{1-4}$ alkyl-OH, —NR$^7$R$^8$ or phenyl optionally substituted with one or two substituents independently selected from halo, $C_{1-4}$ alkyl, halo-substituted $C_{1-4}$ alkyl, hydroxy, $C_{1-4}$ alkoxy and halo-substituted $C_{1-4}$ alkoxy;

$R^5$ is $C_{1-4}$ alkyl or CF$_3$;

$R^6$ is $C_{1-4}$ alkyl, $C_{3-7}$ cycloalkyl or halo-substituted $C_{1-4}$ alkyl;

$R^7$ and $R^8$ are independently selected from the following:
(a) hydrogen,
(b) $C_{1-6}$ alkyl optionally substituted with a substituent independently selected from halo, hydroxy, $C_{1-4}$ alkoxy, amino, $C_{1-4}$ alkylamino and di-($C_{1-4}$ alkyl) amino, (c) $C_{3-7}$ cycloalkyl optionally substituted with a substituent independently selected from hydroxy, $C_{1-4}$ alkyl and $C_{1-4}$ alkoxy, X is independently selected from halo, $C_{1-4}$ alkyl, halo-substituted $C_{1-4}$ alkyl, $C_{1-4}$ alkoxy, hydroxy, nitro and CN; m is 0, 1 or 2; n is 0, 1 or 2; and r is 1, 2 or 3.

Further preferred compounds of this invention are those of the formula (I) wherein $R^1$ is hydrogen, methyl or ethyl; $R^2$ is C(=O)$R^3$ or SO$_2$$R^4$; Y is a direct bond or methylene; Q is selected from the following:

(Q-c) $C_{3-7}$ cycloalkyl optionally substituted with methyl, ethyl or hydroxy, (Q-d) phenyl optionally substituted with one or two substituents independently selected from halo, $C_{1-4}$ alkyl, halo-substituted $C_{1-4}$ alkyl, hydroxy, $C_{1-4}$ alkoxy, halo-substituted $C_{1-4}$ alkoxy, nitro and amino, (Q-e) a 5-membered monocyclic aromatic group selected from thienyl, furyl, thiazolyl, imidazolyl, pyrrolyl, oxazolyl, pyrazolyl, tetrazolyl and triazolyl, and said monocyclic armomatic group being optionally substituted with one or two substituents independently selected from F, Cl, Br, methyl, ethyl, propyl, CF$_3$, hydroxy, methoxy, ethoxy, CF$_3$O-, amino, methylamino, dimethylamino, hydroxymethyl, hydroxyethyl, hydroxypropyl, hydroxybutyl, methoxylmethyl, methoxyethyl and ethoxymethyl, and (Q-f) a 6-membered monocyclic aromatic group selected from pyridyl, pyrazinyl, pyrimidinyl and pyridazinyl, and said monocyclic armomatic group being optionally substituted with one or two substituents independently selected from F, Cl, Br, methyl, ethyl, propyl, CF$_3$, hydroxy, methoxy, ethoxy, CF$_3$O-, amino, methylamino, dimethylamino, hydroxymethyl, hydroxyethyl, hydroxypropyl, hydroxybutyl, methoxylmethyl, methoxyethyl and ethoxymethyl;

$R^3$ is —OR$^6$, —NR$^7$R$^8$, N(OR$^1$)R$^7$ or a group of formula:

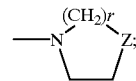

Z is oxygen or NR$^5$;

$R^4$ is methyl, ethyl, propyl, butyl, CF$_3$, hydroxymethyl, hydroxyethyl, hydroxypropyl, hydroxybutyl, amino, methylamino, dimethylamino or phenyl optionally substituted with F, Cl, Br, methyl, ethyl, propyl, CF$_3$, hydroxy, methoxy, ethoxy or CF$_3$O—;

$R^5$ is methyl, ethyl or propyl;

$R^6$ is methyl, ethyl, propyl, butyl, cyclobutyl, cyclopentyl, cyclohexyl or CF$_3$;

$R^7$ and $R^8$ are independently selected from the following:
(a) hydrogen,
(b) methyl, ethyl, propyl, butyl, pentyl, methoxyethyl, methoxymethyl, ethoxyethyl or methoxymethyl, X is F, Cl, Br, methyl, ethyl, isopropyl, CF$_3$, methoxy, nitro or CN; n is 0 or 1; and r is 2.

Also, preferred compounds of this invention are those of the formula (I) wherein $R^1$ is hydrogen or methyl; $R^2$ is C(=O)$R^3$ or SO$_2$$R^4$; Y is a direct bond;
Q is selected from the following:

(Q-c) cyclobutyl, cyclopentyl, cyclohexyl, methylcyclohexyl or cycloheptyl, (Q-d) phenyl optionally substituted with one or two substituents independently selected from F, Cl, Br, methyl, ethyl, propyl, butyl, CF$_3$, hydroxy, methoxy, CF$_3$O—, nitro and amino, (Q-e) thienyl or furyl, and the thienyl and furyl optionally substituted with F, Cl, Br, methyl, ethyl, propyl, $CF_3$, hydroxy, methoxy, ethoxy, $CF_3O$—, amino, methylamino, dimethylamino, hydroxymethyl, hydroxyethyl, hydroxypropyl, hydroxybutyl, methoxylmethtyl, methoxyethyl or ethoxymethyl, and (Q-f) pyridyl optionally substituted with F, Cl, Br, methyl, ethyl, propyl, $CF_3$, hydroxy, methoxy, ethoxy, $CF_3O$—, amino, methylamino, dimethylamino, hydroxymethyl, hydroxyethyl, hydroxypropyl, hydroxybutyl, methoxylmethtyl, methoxyethyl or ethoxymethyl;

$R^3$ is —$OR^6$, —$NR^7R^8$, $N(OR^1)R^7$ or a group of formula:

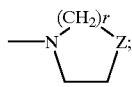

Z is oxygen or $NR^5$;

$R^4$ is methyl, ethyl or propyl, $CF_3$, hydroxyethyl, hydroxypropyl, amino or phenyl optionally substituted with F, Cl, Br, methyl, ethyl, propyl, $CF_3$, hydroxy, methoxy, ethoxy or $CF_3O$—;

$R^5$ is methyl, ethyl or propyl;

$R^6$ is methyl, ethyl, propyl, butyl, cyclobutyl, cyclopentyl, cyclohexyl or $CF_3$;

$R^7$ and $R^8$ are independently selected from the following:

(a) hydrogen, (b) methyl, ethyl, n-propyl, isopropyl, n-butyl, isobutyl, pentyl, methoxyethyl or methoxymethyl, X is F, Cl, Br, methyl or methoxy; and n is 1.

Among these, preferred compounds of this invention are those of the formula (I) wherein Q is selected from the following:

(Q-c) cyclohexyl, (Q-d) phenyl optionally substituted with F, Cl, Br, methyl, ethyl, propyl, methoxy, nitro or $CF_3$, (Q-e) furyl optionally substituted with methyl, ethyl, propyl, hydroxymethyl, hydroxyethyl, hydroxypropyl, hydroxybutyl, methoxylmethtyl, methoxyethyl or ethoxymethyl, and (Q-f) pyridyl optionally substituted with F, Cl, Br, methyl, ethyl, propyl, $CF_3$, hydroxy, methoxy, ethoxy or $CF_3O$—;

$R^3$ is —$OR^6$, —$NR^7R^8$, $N(OR^1)R^7$ or a group of formula:

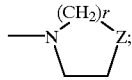

Z is oxygen or $NR^5$;

$R^4$ is methyl, ethyl, propyl or phenyl optionally substituted with methyl or ethyl;

$R^5$ is methyl or ethyl $R^6$ is methyl, ethyl or propyl;

$R^7$ and $R^8$ are independently selected from the following:

(a) hydrogen, (b) methyl, ethyl, n-propyl, isopropyl, n-butyl, isobutyl, pentyl, methoxyethyl or methoxymethyl, X is F, Cl or Br; and n is 1.

Further preferred compounds of this invention are those of the formula (I) wherein Q is cyclohexyl, chlorophenyl, bromophenyl, methylphenyl, nitrophenyl, hydroxymethylfuryl, methylpyridyl, chloropyridyl or methoxypyridyl $R^3$ is methoxy, ethoxy, amino, methylamino, ethylamino, propylarnino, isobutylamino, methoxylethylamino, dimethylamino, diethylamino, —$N(CH_3)C_2H_5$, —$N(CH_3)C_3H_7$, isopropylamino, —$N(OH)CH_3$, —$N(OCH_3)CH_3$, —$N(CH_2CH_2OCH_3)CH_3$, 4-morpholine or 4-methylpiperazinyl;

$R^4$ is methyl, propyl or methylphenyl; and X is F or Cl.

Preferred individual compounds of this invention are:

methyl N-(2-benzoyl-6-chloro- 1H-indol-3-yl)carbamate;

ethyl N-(2-benzoyl-6-chloro- 1H-indol-3-yl)carbamate;

ethyl N-[6-chloro-2-(3-methylbenzoyl)-1H-indol-3-yl] carbamate;

ethyl N-[6-chloro-2-(3-chlorobenzoyl)-1H-indol-3-yl] carbamate;

N-(2-benzoyl-6chloro- 1H-indol-3-yl)urea;

N-[6-chloro-2-(3-methylbenzoyl)- 1H-indol-3-yl]urea;

N-(2-benzoyl-6-chloro-1H-indol-3-yl)-N'-ethylurea;

N-(2-benzoyl-6-chloro-1H-indol-3-yl)-N'-methylurea;

N-(2-benzoyl-6-chloro-1H-indol-3-yl)-N'-propylurea;

N-(2-benzoyl-6-chloro-1H-indol-3-yl)-N'-isobutylurea;

N-(2-benzoyl-6-chloro-1H-indol-3-yl)-N'-(2-methoxyethyl) urea;

N-(2-benzoyl-6-chloro-1H-indol-3-yl) 4morpholinecarboxamide;

N'-[6-chloro-2-(3-chlorobenzoyl)-1H-indol-3-yl]-N,N-dimethylurea;

N'-[6-chloro-2-(3-chlorobenzoyl)-1H-indol-3-yl]-N-hydroxy-N-methylurea;

N-(2-benzoyl-6-chloro-1H-indol-3-yl)-N'-isopropylurea;

N'-(2-benzoyl-6-chloro-1H-indol-3-yl)N,N-dimethylurea;

N'-(2-benzoyl-6-chloro-1H-indol-3-yl)-N,N-diethylurea;

N'-(2-benzoyl-6-chloro-1H-indol-3-yl)-N-ethyl-N-methylurea;

N'-(2-benzoyl-6-chloro-1H-indol-3-yl)-N-methyl-N-propylurea,

N'-(2-benzoyl-6-chloro-1H-indol-3-yl)N-(2-methoxyethyl)-N-methylurea;

N-(2-benzoyl-6-chloro-1H-indol-3-yl)4-methyl- 1-piperazinecarboxamide;

N'-(2-benzoyl-6-chloro-1H-indol-3-yl)-N-hydroxy-N-methylurea;

N'-(2-benzoyl-6-chloro-1H-indol-3-yl)-N-methoxy-N-methylurea;

N'-[6-chloro-2-(3-methylbenzoyl)1H-indol-3-yl]-N,N-dimethylurea;

N'-[6-chloro-2-(3-methylbenzoyl)-1H-indol-3-yl]-N-hydroxy-N-methylurea;

N'-[6-chloro-2-(cyclohexylcarbonyl)-1H-indol-3-yl]-N-methoxy-N-methylurea;

N'-[6-chloro-2-(3-hydroxymethyl-2-furoyl)-1H-indol-3-yl]-N-methoxy-N-methylurea;

N'-[6-chloro-2-(3-hydroxymethyl-2-furoyl)-1H-indol-3-yl]-N,N-dimethylurea);

N'-[6-chloro-2-[(4-methyl-2-pyridinyl)carbonyl]-1H-indol-3-yl]-N-methoxy-N-methylurea;

N'-[6-chloro-2-[(4-chloro-2-pyridinyl)carbonyl]-1H-indol-3-yl]-N-methoxy-N-methylurea;

N'-[6-chloro-2-(3-chlorobenzoyl)-1H-indol-3-yl]-N-methoxy-N-methylurea;

N'-[6-chloro-2-[(4-methoxy-2-pyridinyl)carbonyl]-1H-indol-3-yl]-N-methoxy-N-methylurea;

N-(2-benzoyl-6-chloro-1H-indol-3-yl)methansulfonamide;

N-(2-benzoyl-6-chloro-1H-indol-3-yl)propansulfonamide;

N-(2-benzoyl-6-chloro-1H-indol-3-yl) 4methylbenzenesulfonamide);

N-[6-chloro-2-(3-methylbenzoyl)-1H-indol-3-yl] methanesulfonamide;

N-[6-chloro-2-(3-methylbenzoyl)-1H-indol-3-yl] methanesulfonamide;

N-[6-chloro-2-(3-chlorobenzoyl)-1H-indol-3-yl]methanesulfonamide;
N-[2-(3-bromobenzoyl)-6-chloro-1H-indol-3-yl]methanesulfonamide;
N-(2-benzoyl-6-fluoro-1H-indol-3-yl)methanesulfonamide; and
N-[5-chloro-2-(3-chlorobenzoyl)-1H-indol-3-yl]methanesulfonamide.

More preferred individual compounds of this invention are:
ethyl N-(2-benzoyl-6-chloro-1H-indol-3-yl)carbamate;
N-(2-benzoyl-6-chloro-1H-indol-3-yl)urea;
N-[6-chloro-2-(3-methylbenzoyl)- 1H-indol-3-yl]urea;
N-(2-benzoyl-6chloro-1H-indol-3-yl)N'-ethylurea;
N-(2-benzoyl-6-chloro-1H-indol-3-yl)-N'-methylurea;
N-(2-benzoyl-6-chloro-1H-indol-3-yl)-N'-propylurea;
N-(2-benzoyl-6-chloro-1H-indol-3-yl)-N'-sobutylurea;
N-(2-benzoyl-6-chloro-1H-indol-3-yl)-N'-(2-methoxyethyl)urea;
N'-[6-chloro-2-(3-chlorobenzoyl)-1H-indol-3-yl]-N,N-dimethylurea;
N'-[6-chloro-2-(3-chlorobenzoyl)-1H-indol-3-yl]-N-hydroxy-N-methylurea;
N-(2-benzoyl-6-chloro-1H-indol-3-yl)-N'-isopropylurea;
N'-(2-benzoyl-6-chloro-1H-indol-3-yl)-N,Nimethylurea;
N'-(2-benzoyl-6-chloro-1H-indol-3-yl)-N,N-diethylurea;
N'-(2-benzoyl-6-chloro-1H-indol-3-yl)-N-methyl-N-propylurea;
N'-(2-benzoyl-6-chloro-1H-indol-3-yl)-N-hydroxy-N-methylurea;
N'-(2-benzoyl-6-chloro-1H-indol-3-yl)-N-methoxy-N-methylurea;
N'-[6-chloro-2-(3-methylbenzoyl)-1H-indol-3-yl]-N,N-dimethylurea;
N'-[6-chloro-2-(3-hydroxymethyl-2-furoyl)-1H-indol-3-yl]-N-methoxy-N-methylurea;
N'-[6-chloro-2-[(4-methyl-2-pyridinyl)carbonyl]-1H-indol-3-yl]-N-methoxy-N-methylurea;
N'-[6-chloro-2-[(4-chloro-2-pyridinyl)carbonyl]-1H-indol-3-yl]-N-methoxy-N-methylurea;
N'-[6-chloro-2-[(4-methoxy-2-pyridinyl)carbonyl]-1H-indol-3-yl]-N-methoxy-N-methylurea;
N-(2-benzoyl-6-chloro-1H-indol-3-yl)methanesulfonamide;
N-(2-benzoyl-6-chloro-1H-indol-3-yl)propanesulfonamide;
N-[6-chloro-2-(3-methylbenzoyl)-1H-indol-3-yl]methanesulfonamide;
N-[6-chloro-2-(3-chlorobenzoyl)-1H-indol-3-yl]methanesulfonamide;
N-[2-(3-bromobenzoyl)-6-chloro-1H-indol-3-yl]methanesulfonamide;
N-(2-benzoyl-6-fluoro-1H-indol-3-yl)methanesulfonamide; and
N-[5-chloro-2-(3-chlorobenzoyl)-1H-indol-3-yl]methanesulfonamide.

Most preferred individual compounds are:
N-(2-benzoyl-6-chloro-1H-indol-3-yl)urea;
N-[6-chloro-2-(3-methylbenzoyl)-1H-indol-3-yl]urea;
N'-(2-benzoyl-6-chloro-1H-indol-3-yl)-N-methoxy-N-methylurea;
N'-[6-chloro-2-(3-hydroxymethyl-2-furoyl)-1H-indol-3-yl]-N-methoxy-N-methylurea;
N-(2-benzoyl-6-chloro-1H-indol-3-yl)methanesulfonamide;
N-[6-chloro-2-(3-methylbenzoyl)-1H-indol-3-yl]methanesulfonamide;
N-[6-chloro-2-(3-chlorobenzoyl)-1H-indol-3-yl]methanesulfonamide; and
N-[2-(3-bromobenzoyl)-6-chloro-1H-indol-3-yl]methanesulfonamide.

GENERAL SYNTHESIS

A compound of general formula (I) may be prepared by any synthetic procedure applicable to structure-related compounds known to those skilled in the art. The following representative examples as described hereinafter are illustrative of the invention in which, unless otherwise stated, L, Q, X, Y, $R^1$, $R^2$ and n are as defined herein before.

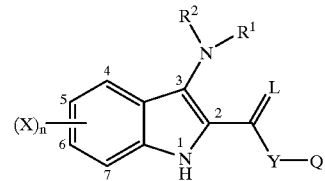

In one embodiment, a compound of the formula (IV) is prepared according to the reaction steps outlined in Scheme 1.

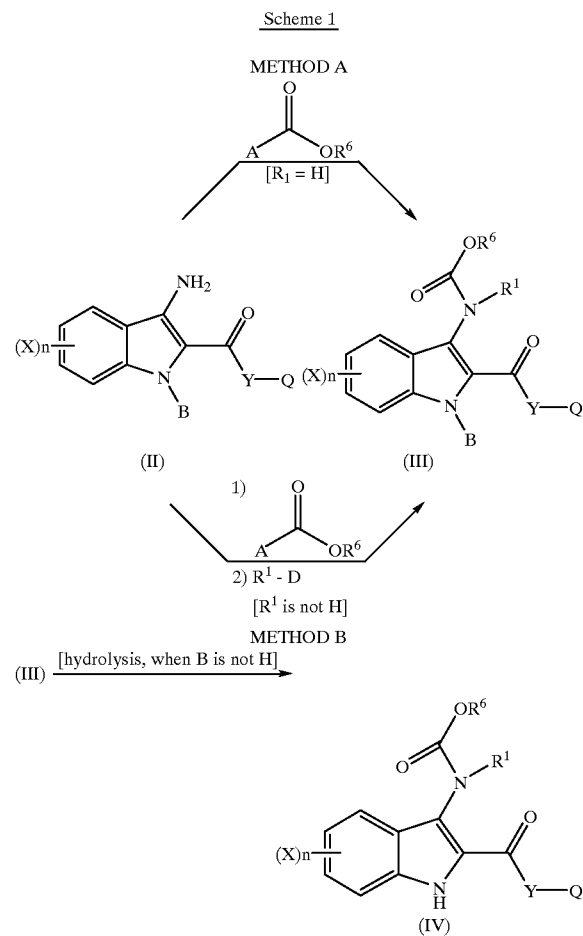

Scheme 1

In Scheme 1, B is hydrogen or a suitable protecting group, for example, methoxycarbonyl, ethoxycarbonyl, tert-butoxycarbonyl (Boc), benzyloxycarbonyl, phenylsulfonyl or p-toluenesulfonyl, or the like. The group $R^1$, $R^6$, X, Y, Q and n are as defined as herein before.

For example, Method A or in step 1 of Method B, a compound of formula (II) is reacted with a compound of formula R⁶OC(O)-A wherein A is defined such that the compound of R⁶OC(O)-A is, for example, a carboxylic acid chloride, a carboxylic acid, a carboxylic acid ester, a carboxylic acid anhydride, or the like. In the instant example, when a compound of formula R⁶OC(O)-A is, for example, a carboxylic acid chloride or carboxylic acid anhydride the reactants may be heated together in the absence or presence of a reaction inert solvent Preferred reaction inert solvents include, but are not limited to, benzene, toluene, xylene, o-dichlorobenzene, nitrobenzene, 1,2dichloroethane, or the like. Preferably, the reaction conducted in the presence of base. A preferred base is selected from, for example, but not limited to, an alkali or alkaline earth metal hydroxide, alkoxide, carbonate, or hydride, such as sodium hydroxide, potassium hydroxide, sodium methoxide, sodium ethoxide, potassium tert-butoxide, sodium carbonate, potassium carbonate, sodium hydride or potassium hydride, or an amine such as triethylamine, tributylamine, diisopropylethylamine, pyridine or dimethylaminopyridine in the presence or absence of a reaction inert solvent Preferred reaction inert solvents include, but are not limited to, benzene, toluene, xylene, o-dichlorobenzene, nitrobenzene, pyridine, dichloromethane, 1,2-dichloroethane, tetrahyrofuran, or mixtures thereof. Reaction temperatures are generally in the range of −100 to 250° C., preferably in the range of 0 to 150° C., but if necessary, lower or higher temperature can be employed. Reaction times are, in general, from several minutes to a day, preferably from 20 minutes to 5 hours, however shorter or longer reaction times, if necessary, can be employed.

Alternatively, when a compound of formula R⁶OC(O)-A is, for example, a carboxylic acid, the intermediate amide obtained from either Method A or step 1 in Method B can be readily prepared by treating the requisite carboxylic acid with a compound of formula (II) in the presence of a coupling reagent such as, but not limited to, 1-(dimethylarninopropyl)-3-ethylcarbodiimide (WSC), N,N'-dicyclohexylcarbodiimidazole (DCC), carbonyldiimidazole, cyanophosphonic acid diethyl ester, or the like. Preferred reaction inert solvents include, but are not limited to, acetone, acetonitrile, dichloromethane, 1,2-dichloroethane, N,N-dimethylformamide, N,N-dimethylacetamide, dimethylsulfoxide, dioxane, tetrahyrofuran or pyridine. Or, for example, under Mitsunobu-type reaction conditions. A suitable condensing reagent in the Mitsunobu reaction is a di-(C₁₋₄)alkyl azodicarboxylate in the presence of a triarylphosphine, for example, diethyl azodicarboxylate in the presence of triphenylphosphine. Reaction inert solvents of choice include tetrahydrofuran, dichloromethane, dimethylformamide, benzene, toluene, or the like. The reaction temperature is preferably in the range of 0° C. to reflux temperature of the solvent, e.g. 0 to 100° C., but if necessary, temperatures lower or higher can be adopted. Reaction times are, in general, from several minutes to a day, preferably from 20 minutes to 5 hours, however shorter or longer reaction times, if necessary, can be employed.

In step 2 of Method B, the intermediate amide (the group B is a suitable protecting group as defined herein above) is reacted with a compound of formula R¹-D wherein D is a selected from a suitable displaceable group, for example, a halo or sulfonyloxy group, for example, fluoro, chloro, bromo, iodo, trifluoromethanesulfonyloxy, methanesulfonyloxy, benzenesulfonyloxy or p-toluenesulfonyloxy group. Preferably, the instant reaction is conducted in the presence of a suitable base, for example, an alkali or alkaline earth metal alkoxide, carbonate, or hydride, such as, but not limited to, sodium methoxide, sodium ethoxide, potassium tert-butoxide, sodium carbonate, potassium carbonate, sodium hydride or potassium hydride. Preferred reaction inert solvents include, but are not limited to, acetone, acetonitrile, N,N-dimethylformamide, N,N-dimethylacetamide, dimethylsulfoxide, dioxane, tetrahydrofuran or pyridine. Reaction temperatures are preferably in the range of −100 to 250° C., usually in the range of 0° C. to reflux temperature of solvent, but if necessary, lower or higher temperature can be employed. Reaction time is in general from several minutes to a day, preferably from 30 minutes to 5 hours, however shorter or longer reaction times, if necessary, can be employed.

When the group B is a suitable protecting group as defined herein above, the group B may be removed by a number of standard procedures known to those skilled in the art (for example, see "Protection of the Amino Group", in *Protective Groups in Organic Synthesis,* 2nd Edition, T. W. Greene and P. G. M. Wuts, Ed., John Wiley and Sons, Inc. 1991, pp. 309–405).

A compound of formula (IV) may also be prepared according to the reaction step outlined in Scheme 2.

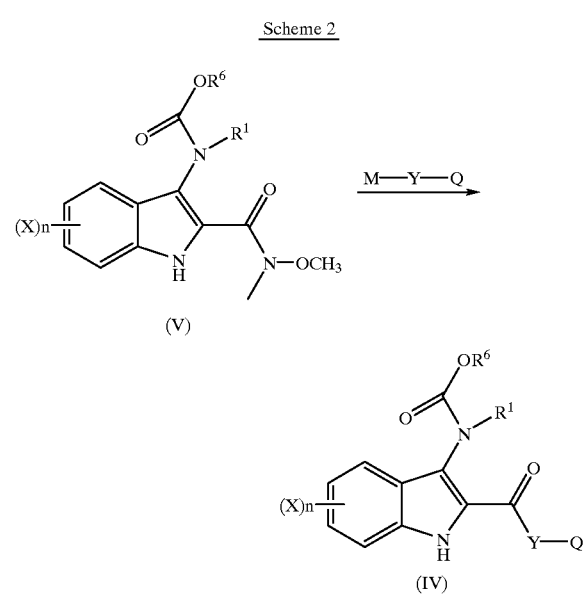

Scheme 2

In Scheme 2, X, Y, Q, R', R⁶ and n are as defined herein before. The compound of formula (V) (amide) is used for illustrative purposes only and is not meant to limit the scope of the present invention. Thus, for example, a compound of formula (V) is treated with a compound of formula M-Y-Q in a reaction inert solvent. In a compound of formula M-Y-Q, M is defined such that compound of formula M-Y-Q is, for example, the corresponding Grignard or alkali metal reagent, for example, M may be magnesium chloride (Q-Y-MgCl), magnesium bromide (Q-Y-MgBr), or magnesium iodide (Q-Y-MgI), lithium (Q-Y-Li), potassium (Q-Y-K) or sodium (Q-Y-Na). The suitable Grignard or alkali metal reagents may be readily prepared, in situ, prior to use from the appropriate starting materials by conventional methods known to those skilled in the art. Preferred reaction inert solvents include, but are not limited to, diethyl ether, tetrahyrofuran, dimethoxyethane, dioxane, benzene, toluene, hexane or cyclohexane, or mixtures thereof Reaction temperatures are preferably in the range of −100 to 150° C., usually in the range of −70° C. to reflux temperature of solvent, preferably, −40° C. to room temperature, but if necessary, lower or higher temperature can be employed. Reaction time is in general from several minutes to a day, preferably from 30 minutes to 5 hours, however shorter or longer reaction times, if necessary, can be employed.

The compound of formula (V) is readily accessible by conventional synthetic methods known to those skilled in the art and, of which, are adequately described within the accompanying non-limiting examples.

In another embodiment, compounds of the formula (VI), compounds of formula (VII) and compounds of formula (IX), wherein $R^1$, $R^6$, $R^7$, R, X, Y, Q, n and r are as defined as herein before, B is a suitable protecting group as herein before, are prepared according to the reaction steps outlined in Scheme 3.

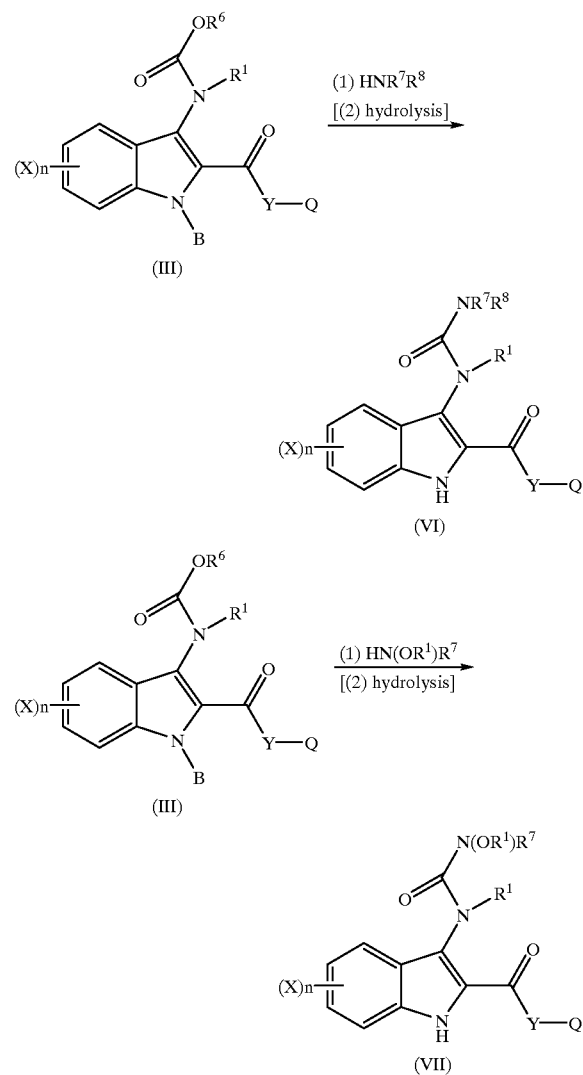

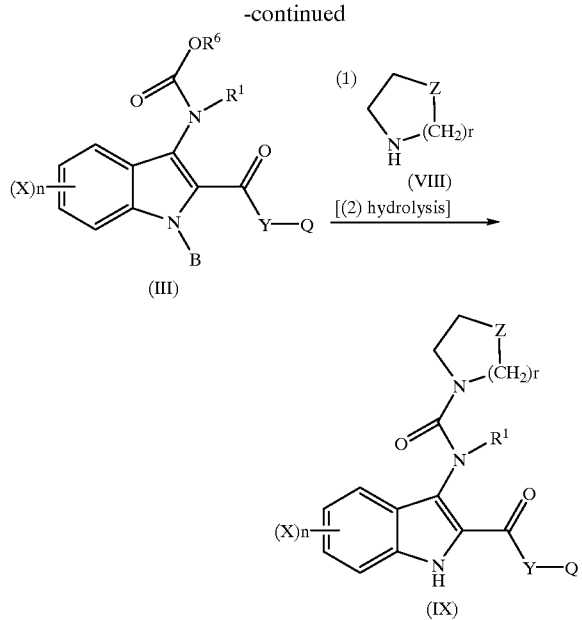

Scheme 3

For example, a compound of formula (III) is reacted with a compound of formula $HNR^7R^8$, a compound of formura $HN(OR^1)R^7$, or a compound of formula (VIII). The reactants may be heated together in the absence or presence of a reaction inert solvent Preferred reaction inert solvents include, but are not limited to, benzene, toluene, xylene, o-dichlorobenzene, nitrobenzene, pyridine, 1,2-dichloroethane, dichloromethane, acetonitrile, dioxane, N,N-dimethylformamide, or the like. If nessesary, the reaction conducted in the presence of base. A preferred base is selected from, for example, but not limited to, an alkali or alkaline earth metal hydroxide or carbonate such as sodium hydroxide, potassium hydroxide, sodium carbonate, potassium carbonate, or an amine such as triethylamine, tributylamine, diisopropylethylamine, pyridine or dimethylaminopyridine in the presence or absence of a reaction inert solvent. Preferred reaction inert solvents include, but are not limited to, benzene, toluene, xylene, o-dichlorobenzene, nitrobenzene, pyridine, dichloromethane, 1,2-dichloroethane, tetrahyrofuran, or mixtures thereof Reaction temperatures are generally in the range of −100 to 250° C., preferably in the range of 0 to 150° C., but if necessary, lower or higher temperature can be employed. Reaction times are, in general, from several minutes to a day, preferably from 20 minutes to 5 hours, however shorter or longer reaction times, if necessary, can be employed.

When the group B is a suitable protecting group as defined herein above, if nesesary, the group B may be removed by a number of standard procedures known to those skilled in the art (for example, see "Protection of the Amino Group", in *Protective Groups in Organic Synthesis,* 2nd Edition, T. W. Greene and P. G. M. Wuts, Ed., John Wiley and Sons, Inc. 1991, pp. 309–405).

In another embodiment, compounds of the formula (X) and compounds of formura (XI), wherein $R^8$, X, Y, Q and n are as defined as herein before, B is a suitable protecting group as herein before, are prepared according to the reaction steps outlined in Scheme 4.

Scheme 4

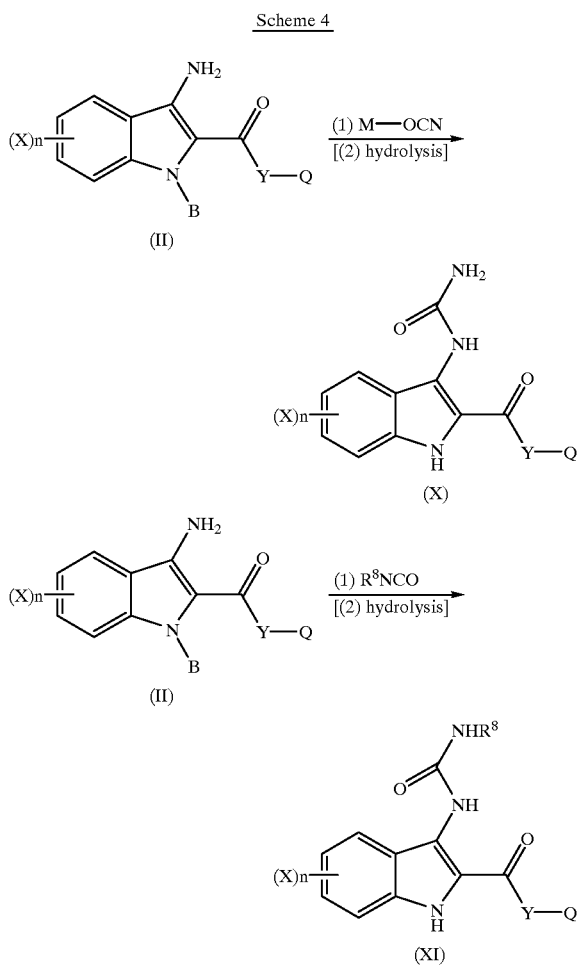

Scheme 4

For example, a compound of formula (II) is reacted with a compound of formula M-OCN, or a compound of formula $R^8NCO$. In a compound of formula M-OCN, M is defined such that compound of formula M-OCN is, for example, the corresponding alkali or alkaline earth metal reagent, for example, M may be sodium, pottasium.

The reactants may be heated together in the absence or presence of a reaction inert solvent. Preferred reaction inert solvents include, but are not limited to, benzene, toluene, xylene, o-dichlorobenzene, nitrobenzene, 1,2-dichloroethane, dichloromethane, or the like. Reaction temperatures are generally in the range of −100 to 250° C., preferably in the range of 0 to 150° C., but if necessary, lower or higher temperature can be employed. Reaction times are, in general, from several minutes to a day, preferably from 20 minutes to 5 hours, however shorter or longer reaction times, if necessary, can be employed.

When the group B is a suitable protecting group as defined herein above, the group B may be removed by a number of standard procedures known to those skilled in the art (for example, see "Protection of the Amino Group", in *Protective Groups in Organic Synthesis*, 2nd Edition, T. W. Greene and P. G. M. Wuts, Ed., John Wiley and Sons, Inc. 1991, pp. 309–405).

In another embodiment, a compound of the formula (XIII) is prepared according to the reaction steps outlined in Scheme 5.

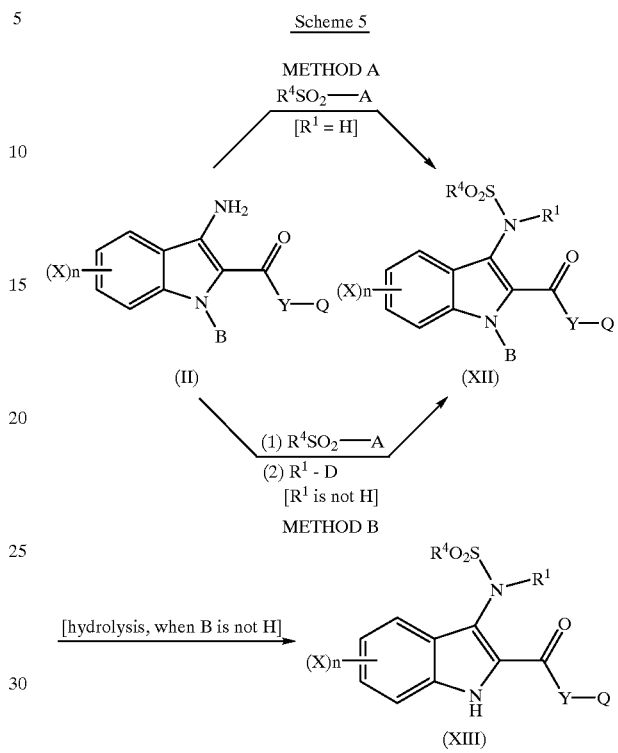

Scheme 5

In Scheme 5, B is hydrogen or a suitable protecting group, for example, methoxycarbonyl, ethoxycarbonyl, tert-butoxycarbonyl (Boc), or benzyloxycarbonyl, or the like. The group Q, X, $R^1$ and n are defined as herein before.

For example, Method A or in step 1 of Method B, a compound of formula (II) is reacted with a compound of formula $R^4SO_2$—A wherein A is defined such that the compound of $R^4SO_2$—A is, for example, a sulfonic acid chloride, a sulfonic acid anhydride, or the like. In the instant example, when a compound of formula $R^4SO_2$-A is, for example, a sulfonic acid chloride the reactants may be heated together in the absence or presence of a reaction inert solvent. Preferred reaction inert solvents include, but are not limited to, benzene, toluene, xylene, o-dichlorobenzene, nitrobenzene, 1,2-dichloroethane, or the like. Preferably, the reaction is conducted in the presence of a base. A preferred base is selected from, for example, but not limited to, an alkali or alkaline earth metal hydroxide, alkoxide, carbonate, or hydride, such as sodium hydroxide, potassium hydroxide, sodium methoxide, sodium ethoxide, potassium tert-butoxide, sodium carbonate, potassium carbonate, sodium hydride or potassium hydride, or an amine such as triethylamine, tributylamine, diisopropylethylamine, pyridine or dimethylaminopyridine in the presence or absence of a reaction inert solvent. Preferred reaction inert solvents include, but are not limited to, benzene, toluene, xylene, o-dichlorobenzene, nitrobenzene, pyridine, dichloromethane, 1,2-dichloroethane, tetrahyrofuran, or mixtures thereof Reaction temperatures are generally in the range of −100 to 250° C., preferably in the range of 0 to 150° C., but if necessary, lower or higher temperature can be employed. Reaction times are, in general, from several minutes to a day, preferably from 20 minutes to 5 hours, however shorter or longer reaction times, if necessary, can be employed. Under the reaction conditions described herein above, the intermediate indole may be isolated as either the mono-substituted sulfonylamino- or di-substituted sulfonylamino-intermediate, or mixtures thereof, and as such, is preferably used in the next step without isolation.

In step 2 of Method B, the intermediate amide (the group B is a suitable protecting group as defined herein above) is reacted with a compound of formula $R^1$-D wherein D is a selected from a suitable displaceable group, for example, a halo or sulfonyloxy group, for example, fluoro, chloro, bromo, iodo, trifluoromethanesulfonyloxy, methanesulfonyloxy benzenesulfonyloxy or p toluenesulfonyloxy group. Preferably, the instant reaction is conducted in the presence of a suitable base, for example, an alkali or alkaline earth metal alkoxide, carbonate, or hydride, such as, but not limited to, sodium methoxide, sodium ethoxide, potassium tert-butoxide, sodium carbonate, potassium carbonate, sodium hydride or potassium hydride. Preferred reaction inert solvents include, but are not limited to, acetone, acetonitrile, N,N-dimethylformamide, N,N-dimethylacetamide, dimethylsulfoxide, dioxane, tetrahydrofuran or pyridine. Reaction temperatures are preferably in the range of −100 to 250° C., usually in the range of 0° C. to reflux temperature of solvent, but if necessary, lower or higher temperature can be employed. Reaction time is in general from several minutes to a day, preferably from 30 minutes to 5 hours, however shorter or longer reaction times, if necessary, can be employed.

When the group B is a suitable protecting group as defined herein above, the group B may be removed by a number of standard procedures known to those skilled in the art (for example, see "Protection of the Amino Group", in *Protective Groups in Organic Synthesis,* 2nd Edition, T. W. Greene and P. G. M. Wuts, Ed., John Wiley and Sons, Inc. 1991, pp. 309–405). Under these reaction conditions, facile cleavage of one of the sulfonyl groups of the di-substituted sulfonylamino- intermediate occurs concomitantly.

A compound of formula (XIII) may also be prepared according to the reaction step outlined in Scheme 6.

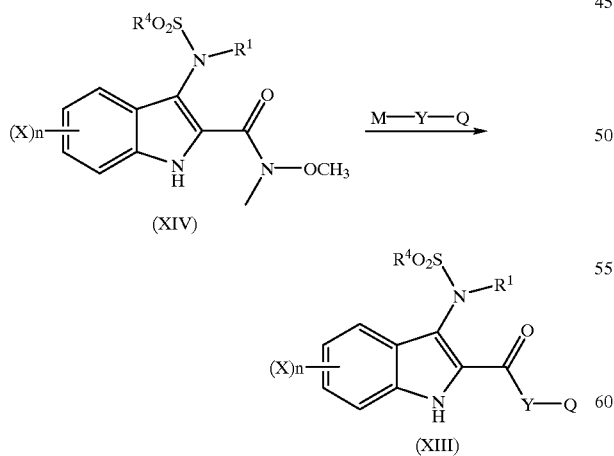

Scheme 6

In Scheme 6, X, Q, $R^1$, $R^4$ and n are as defined herein before. The compound of formula (XIV) (amide) is used for illustrative purposes only and is not meant to limit the scope of the present invention. Thus, for example, a compound of formula (XIV) is treated with a compound of formula M-Y-Q in a reaction inert solvent. In a compound of formula M-Y-Q, M is defined such that compound of formula M-Y-Q is, for example, the corresponding Grignard or alkali metal reagent, for example, M may be magnesium chloride (Q-Y-MgCl), magnesium bromide (Q-Y-MgBr), or magnesium iodide (Q-Y-MgI), lithium (Q-Y-Li), potassium (Q-Y-K) or sodium (Q-Y-Na). The suitable Grignard or alkali metal reagents may be readily prepared, in situ, prior to use from the appropriate starting materials by conventional methods known to those skilled in the art. Preferred reaction inert solvents include, but are not limited to, diethyl ether, tetrahydrofuran, dimethoxyethane, dioxane, benzene, toluene, hexane or cyclohexane, or mixtures thereof Reaction temperatures are preferably in the range of −100 to 150° C., usually in the range of −70° C. to reflux temperature of solvent, preferably, −40° C. to room temperature, but if necessary, lower or higher temperature can be employed. Reaction time is in general from several minutes to a day, preferably from 30 minutes to 5 hours, however shorter or longer reaction times, if necessary, can be employed.

The compound of formula (XIV) is readily accessible by conventional synthetic methods known to those skilled in the art and, of which, are adequately described within the accompanying non-limiting examples.

A compound of formula (II) may be prepared by a number of synthetic procedures known to those skilled in the art. The following representative examples as described hereinafter are illustrative and are not meant to limit the scope of the invention in anyway.

For example, a compound of formula (II), wherein B, X, Y, Q and n are as defined as herein before, is readily accessible from the appropriate 2-aminobenzonitrile (XV) as illustrated in Scheme 7 (For example, see E. E. Garcia, L. E. Benjamin and R. Ian Fryer, *J. Heterocycl. Chem.,* 10, 51(1973)).

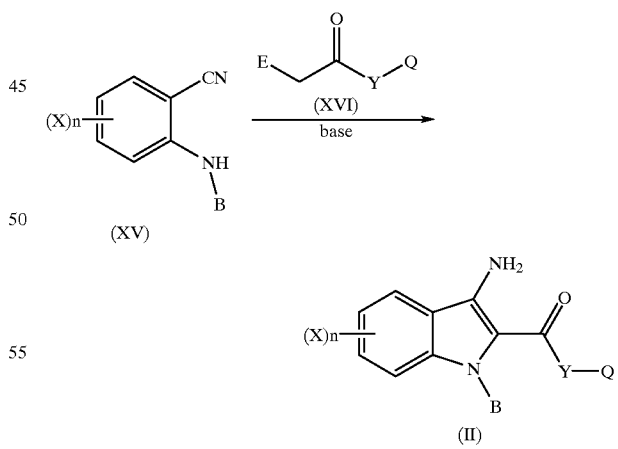

Scheme 7

Thus, the requisite 2-aminobenzonitrile (XV) is reacted with a compound of formula (XVI), wherein Y and Q are as defined as herein before and E is halo, preferably, iodo, bromo or chloro, in the presence of a suitable base. A suitable base is, for example, an alkali or alkaline earth metal alkoxide, carbonate, or hydride, such as, but not limited to, sodium tert-butoxide, potassium tert-butoxide, sodium carbonate, potassium carbonate, sodium hydride or potassium hydride. Preferred reaction inert solvents include, but are not limited to, acetonitrile, N,N-dimethylformamide, N,N-dimethylacetamide, dimethylsulfoxide, dioxane or tetrahydrofuran. Reaction temperatures are preferably in the range of 40 to 250° C., usually in the range of 0° C. to reflux temperature of solvent, but if necessary, lower or higher temperature can be employed. Reaction time is in general from several minutes to a day, preferably from 30 minutes to 5 hours, however shorter or longer reaction times, if necessary, can be employed.

Alternatively, a compound of formula (II), wherein X, Y, Q and n are as defined as herein before and B is hydrogen, may be prepared according to the reaction steps depicted in Scheme 8.

to those skilled in the art and, of which, are adequately described within the accompanying non-limiting examples.

The starting material of the formulae in the aforementioned general syntheses may be obtained by conventional methods known to those skilled in the art. The preparation of such starting materials is described within the accompanying non-limiting examples which are provided for the purpose of illustration only. Alternatively, requisite starting materials may be obtained by analogous procedures, or modifications thereof, to those described hereinafter.

The products which are addressed in the aforementioned general syntheses and illustrated in the experimental examples described herein after may be isolated by standard methods and purification can be achieved by conventional means known to those skilled in the art, such as distillation, crystallization or chromatography techniques.

Certain compounds described herein contain one or more asymmetric centers and are capable of existing in various Scheme 8

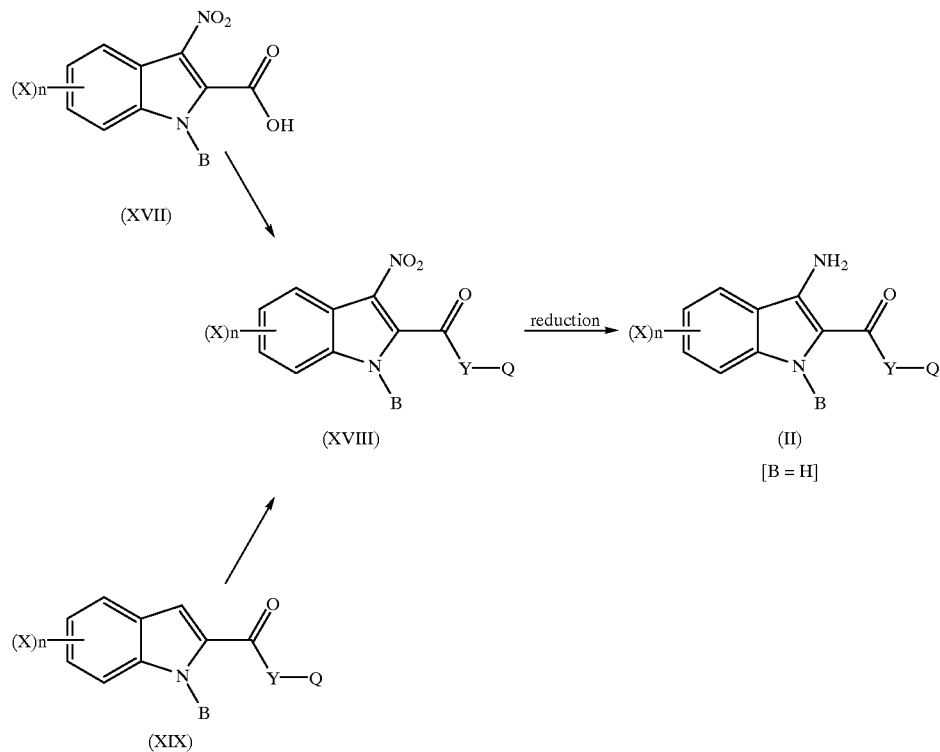

Scheme 8

For example, the compound of formula (II) may be prepared from the requisite nitro compound of formula (XVIII) by reduction in the presence of suitable reducing agent by conventional methods known to those skilled in the art. For example, tin (II) chloride in ethanol (F. D. Bellamy and K. Ou, Tetrahedron Lett., 25, 839 (1984)), iron—ammonium chloride in aqueous ethanol (K. Ramadas and N. Srinivasan, Synth. Commun., 22, 3189 (1992)), or zinc dust or iron in acetic acid (E. Wertheim, Org. Synth. Coll. Vol. 2., 160 (1943)), or by catalytic hydrogenolysis. Preferred catalysts are, for example, palladium-on-charcoal or Raney-Nickel (C. F. H. Allen and J. Vanallan, Org. Synth. Coll. Vol. 3., 63 (1955)). The nitro compound of formula (XVIII) is readily accessible by conventional synthetic methods known stereoisomeric forms. The present invention contemplates all such possible steremers as well as their racemic and resolved, enantiomerically pure forms and pharmaceutically acceptable salts thereof.

Certain compounds of the present invention are capable of forming addition salts with inorganic or organic acids. The pharmaceutically acceptable acid salts of the compounds of formula (I) are those which form non-toxic addition salts, such as, but not limited to, the hydrochloride, hydrobromide, sulfate or bisulfate, acetate, benzoate, besylate, citrate, flimarate, glucuronate, hippurate, lactate, tartrate, saccharate, succinate, maleate, methanesulfonate, p-toluenesulfonate, phosphate and pamoate (i.e., 4,4'-methylene-bis-(3-hydroxy-2-naphthoate)) salts. The pharmaceutically acceptable acid salts may be prepared by conventional techniques.

Certain compounds of the present invention are capable of forming pharmaceutically acceptable non-toxic cations. Pharmaceutically acceptable non-toxic cations of compounds of formula (I) may be prepared by conventional techniques by, for example, contacting said compound with a stoichiometric amount of an appropriate alkaline or alkaline earth metal (sodium, potassium, calcium and magnesium) hydroxide or alkoxide in water or an appropriate organic solvent such as ethanol, isopropanol, mixtures thereof, or the like.

Also included within the scope of this invention are bioprecursors (also called pro-drugs) of the compounds of the formula (I). A bioprecursor of a compound of the formula (I) is a chemical derivative thereof which is readily converted back into the parent compound of the formula (I) in biological systems. In particular, a bioprecursor of a compound of the formula (I) is converted back to the parent compound of the formula (I) after the bioprecursor has been administered to, and absorbed by, a mammalian subject, e.g., a human subject. When the compounds of the formula (I) of this invention may form solvates such as hydrates, such solvates are included within the scope of this invention.

An example of prodrug of the compound of formula (I) is a compound of the formula (I), wherein the 1st position of indole ring is substituted with a group selected from hydroxymethyl, —C(O)—$C_{1-4}$ alkyl, —C(O)—(NH$_2$)CH—($C_{1-4}$ alkyl), —C(O)-phenyl, —CH$_2$NHC(O)-azyl, —CH$_2$—CH$_{1-4}$ alkyl-O—C(O)-$C_{1-4}$ alkyl, —$C_{1-4}$ alkyl-pyridyl, —C(O)CH$_2$NR$_2$ and —CH$_2$N($C_{1-4}$ alkyl)$_2$.

Another example of prodrug of the compound of formula (I) is a compound of the formula (I), wherein the carboxyl group is substituted with a group selected from $C_{1-4}$ alkyl, —CH$_2$-$C_{1-4}$ alkyl-O—C(O)$C_{1-4}$ alkyl, —CH$_2$-$C_{1-4}$ alkyl-O—C(O)—N($C_{1-4}$ alkyl)$_2$, —CH$_2$C(O)—N($C_{1-4}$ alkyl)$_2$, —CH$_2$-$C_{1-4}$ alkyl-O—C(O)-O—$C_{1-4}$ alkyl, ethyl-OH and —CH$_2$CO$_2$H.

The compounds of the formula (I) of this invention can be administered via either the oral, parenteral or topical routes to mammals In general, these compounds are most desirably administered to humans in doses ranging from 0.01 mg to 100 mg per kg of body weight per day, although variations will necessarily occur depending upon the weight, sex and condition of the subject being treated, the disease state being treated and the particular route of administration chosen. However, a dosage level that is in the range of from 0.01 mg to 10 mg per kg of body weight per day, single or divided dosage is most desirably employed in humans for the treatment of abovementioned diseases.

The compounds of the present invention may be administered alone or in combination with pharmaceutically acceptable carriers or diluents by either of the above routes previously indicated, and such administration can be carried out in single or multiple doses. More particularly, the novel therapeutic agents of the invention can be administered in a wide variety of different dosage forms, i.e., they may be combined with various pharmaceutically acceptable inert carriers in the form of tablets, capsules, lozenges, trochees, hard candies, powders, sprays, creams, salves, suppositories, jellies, gels, pastes, lotions, ointments, aqueous suspensions, injectable solutions, elixirs, syrups, and the like. Such carriers include solid diluents or fillers, sterile aqueous media and various nontoxic organic solvents, etc. Moreover, oral pharmaceutical compositions can be suitably sweetened and/or flavored. In general, the therapeutically-effective compounds of this invention are present in such dosage forms at concentration levels ranging 5% to 70% by weight, preferably 10% to 50% by weight.

For oral administration, tablets containing various excipients such as microcrystalline cellulose, sodium citrate, calcium carbonate, dipotassium phosphate and glycine may be employed along with various disintegrants such as starch and preferably corn, potato or tapioca starch, alginic acid and certain complex silicates, together with granulation binders like polyvinylpyrrolidone, sucrose, gelatin and acacia. Additionally, lubricating agents such as magnesium stearate, sodium lauryl sulfate and talc are often very useful for tabletting purposes. Solid compositions of a similar type may also be employed as fillers in gelatine capsules; preferred materials in this connection also include lactose or milk sugar as well as high molecular weight polyethylene grycols. When aqueous suspensions and/or elixirs are desired for oral administration, the active ingredient may be combined with various sweetening or flavoring agents, coloring matter or dyes, and, if so desired, emulsifying and/or suspending agents as well, together with such diluents as water, ethanol, propylene glycol, glycerin and various combinations thereof.

For parenteral administration, solutions of a compound of the present invention in either sesame or peanut oil or in aqueous propylene glycol may be employed. The aqueous solutions should be suitably buffered (preferably pH>8) if necessary and the liquid diluent first rendered isotonic. These aqueous solutions are suitable for intravenous injection purposes. The oily solutions are suitable for intra-articular, intramuscular and subcutaneous injection purposes. The preparation of all these solutions under sterile conditions is readily accomplished by standard pharmaceutical techniques well-known to those skilled in the art. Additionally, it is also possible to administer the compounds of the present invention topically when treating inflammatory conditions of the skin and this may preferably be done by way of creams, jellies, gels, pastes, ointments and the like, in accordance with standard pharmaceutical practice.

The compounds of formula (I) may also be administered in the form of suppositories for rectal or vaginal administration of the active ingredient. These compositions can be prepared by mixing the active ingredient with a suitable non-irritating excipient which is solid at room temperature (for example, 10° C. to 32° C.) but liquid at the rectal temperature and will melt in the rectum or vagina to release the active ingredient. Such materials are polyethylene glycols, cocoa butter, suppository and wax.

For buccal administration, the composition may take the form of tablets or lozenges formulated in conventional manner.

Combination with Other Drugs

Compounds of Formula I would be useful for, but not limited to, the treatment of inflammation in a subject, and for treatment of other inflammation-associated disorders, such as, as an analgesic in the treatment of pain and headaches, or as an antipyretic for the treatment of fever. For example, combinations of the invention would be useful to treat arthritis, including but not limited to rheumatoid arthritis, spondyloarthopathies, gouty arthritis, osteoarthritis, systemic lupus erythematosus and juvenile arthritis. Such combinations of the invention would be useful in the treatment of asthma, bronchitis, inmenstrual cramps, tendinitis, bursitis, and skin related conditions such as psoriasis, eczema, burns and dermatitis. Combinations of the invention also would be useful to treat gastrointestinal conditions such as inflammatory bowel disease. Crohn's disease, gastritis, irritable bowel syndrome and ulcerative colitis and for the prevention of colorectal cancer. Combinations of the invention would be useful in creating inflammation in such diseases as vascular diseases, migraine headaches, periarteritis nodosa, thyroiditis, aplastic anemia, Hodgkin's disease, sclerodoma, rheumatic fever, type I diabetes, myasthenia gravis, multiple sclerosis, sarcoidosis, nephrotic syndrome, Behcet's syndrome, polymyositis, gingivitis, hypersensitivity, Conjunctivitis, swelling occurring after injury, myocardial ischemia, and the like. The combinations would also be useful for the treatment of certain central nervous system disorders such as Alzheimer's disease and dimentia. The combinations of the invention are useful as anti-inflammatory agents, such as for the treatment of arthritis, with the additional benefit of having significantly less harmful side effects. These compositions would also be useful in the treatment of allergic rhinitis, respiratory distress syndrome, endotoxin shock syndrome, atherosclerosis and central nervous system damage resulting from stroke, ischemia and trauma.

Compounds of formula (I) will be useful as a partial or complete substitute for conventional NSAID's in preparations wherein they are presently co-administered with other agents or ingredients. Thus, the invention encompasses pharmaceutical compositions for treating COX-2 mediated diseases as defined above comprising a non-toxic therapeutically effective amount of the compound of formula (I) and one or more ingredients such as another pain reliever including acetaminophen or phenacetin; a potentiator including caffeine; an $H_2$-antagonist, aluminom or magnesium hydroxide, simethicone, a decongestant including phenylephrine, phenylproanolamnine, psuedophedrine, oxymetazoline, ephinephrine, naphazoline, xylometazoline, propylhexedrine, or levodesoxyephedrine; an antuitussive including codeine, hydrocodone, caramiphen, carbetapentane, or dextramethorphan; a prostaglandin including misoprostol, enprostil, rioprostil, ornoprotol or rosaprostol; a diuretic; a sedating or non-sedating antihistamine; anticancer agents such as angiostatin and endostatin; anti-Alzheimers such as Doepezil and Tacrine hydrochloride; and TNF alpha inhibitors such as Etanercept.

These cyclooxygenase inhibitors can further be used in combination with a nitric oxide inhibitors disclosed in WO 96/28145.

Also, the invention encompasses pharmaceutical compositions for treating COX-2 mediated diseases as defined above comprising a non-toxic therapeutically effective amount of the compound of formula (I) and one or more anti-ulcer agent and/or prostaglandins, which are disclosed in WO 97/11701.

The useful prostaglandins include misoprostol, plusminus methyl 11α, 16-dihydroxy-16-methyl-9-oxoprost 13E-en-1-oate; enisoprost and methyl-7-[2B-[6-(1-cyclopenten-1-yl)-4-hydroxy-4-methyl-1E, 5E-hexadienyl]-3α-hydroxy-5-oxo 1R, 1α-cyclopentyl]-4Z-heptenoate. Prostaglandins within the scope of the invention also include arbaprostil, enprostil, rioprostol, nocloprost, mexiprostil, ornoprostol, dimoxaprost, tiprostanide and rosaprostol.

The present compounds may also be used in co-therapies, partially or completely, in place of other conventional antiinflammatories, such as together with steroids, 5-lipoxygenase inhibitors, $LTB_4$ antagonists and $LTA_4$ hydrolase inhibitor's.

An example of $LTB_4$ is disclosed in W097/29774. Suitable $LTB_4$ inhibitors include, among others, ebselen, Bayer Bay-x-1005, Ciba Geigy compound CGS-25019C, Leo Denmark compound ETH-615, Lilly compound LY-293111, Ono compound ONO-4057, Terumo compound TMK-688, Lilly compounds LY-213024, 264086 and 292728, Ono compound ONO-LB457, Searle compound SC-S3228, calcitrol, Lilly compounds LY-210073, LY223982, LY233469, and LY255283, Ono compound ONO-LB-448, Searle compounds SC41930, SC-50605 and SC-51146, and SK&F compound SKF-104493. Preferably, the $LTB_4$ inhibitors are selected from ebselen, Bayer Bay-x-1005, Ciba Geigy compound CGS-25019C, Leo Denmark compound ETH-61S, Lilly compound LY-2931 11, Ono compound ONO-4057 and Terumo compound TMK-688.

An example of 5-LO inhibitors is disclosed in W097/29776. Suitable 5-LO inhibitors include, among others, masoprocol, tenidap, zileuton, pranlukast, tepoxalin, rilopirox, flezelastine hydrochloride, enazadrem phosphate and bunaprolast.

An example of $LTA_4$ hydrolase inhibitors is disclosed in W097/29774. Suitable $LTA_4$ hydrolase inhibitors include, among others, Rhone-Poulenc Rorer RP-64966.

The administration of the present invention may be for either prevention or treatment purposes. The methods and compositions used herein may be used alone or in conjunction with additional therapies known to those skilled in the art in the prevention or treatment of angiogenesis. Alternatively, the methods and compositions described herein may be used as adjunct therapy. By way of example, the cyclooxygenase-2 inhibitor may be administered alone or in conjunction with other antineoplastic agents or other growth inhibiting agents or other drugs or nutrients.

There are large numbers of antineoplastic agents available in commercial use, in clinical evaluation and in pre-clinical development, which could be selected for treatment of angiogenesis by combination drug chemotherapy. Such antineoplastic agents fall into several major categories, namely, antibiotic-type agents, alkylating agents, antimetabolite agents, hormonal agents, immunological agents, interferon-type agents and a category of miscellaneous agents. Alternatively, other anti-neoplalstic agents, such as metallomatrix proteases inhibitors (MMP), such as MMP-13 inhibitors including batiastat, marimastat. Agouron Pharmaceuticals AG-3340, and Roche RO-32-3555, or alpha,beta, inhibitors may be used.

A first family of antineoplastic agents which may be used in combination with a selective cyclooxygenase-2 inhibitor consists of antimetabolite-type antineoplastic agents. Suitable antimetabolite antineoplastic agents may be selected from the group consisting of 5-FU-fibrinogen, acanthifolic acid, aminothiadiazole, brequinar sodium, carmofur, Ciba-Geigy CGP-30694, cyclopentyl cytosine, cytarabine phosphate stearate, cytarabine conjugates, Lilly DATHF, Merrel Dow DDFC, dezaguanine, dideoxycytidine, dideoxyguanosine, didox, Yoshitomi DMDC, doxifluridine, Wellcome EHNA, Merck & Co. EX-015, fazarabine, floxuridine, fludarabine phosphate, 5-fluorouracil, N-(2'-furanidyl)-5-fluorouracil, Daiichi Seiyaku OF-152, isopropyl pyrrolizine, Lilly LY-188011, Lilly LY-264618, methobenzaprim, methotrexate, Wellcome MZPES. norspermidine, NCI NSC-127716, NCI NSC-264880, NCI NSC-39661, NCI NSC-612567, Warner-Lambert PALA, pentostatin, piritrexim, plicamycin, Asahi Chemical PL-AC, Takeda TAC-788, thioguanine, tiazofurin, Erbamont TIF, trimetrexate, tyrosine kinase inhibitors, tyrosine protein kinase inhibitors, Taiho UFT and uricytin.

A second family of antineoplastic agents which may be used in combination with a selective cyclooxygenase-2 inhibitor consists of alkylating-type antineoplastic agents. Suitable alkylating-type antineoplastic agents may be selected from the group consisting of Shionogi 254-S, aldo-phosphamide analogues, altretamine, anaxirone, Boehringer Mannheim BBR-2207, bestrabucil, budotitane, Wakunaga CA-102, carboplatin, carmustine, Chinoin-139, Chinoin-153, chlorambucil, cisplatin, cyclophosphamide, American Cyanamid CL-286558, Sanofi CY-233, cyplatate, Degussa D-19-384, Sumimoto DACHP(Myr)2, diphenylspiromustine, diplatinum cytostatic. Erba distamycin derivatives, Chugai DWA-2114R, ITI E09, elmustine, Erbamont FCE-24517, estramustine phosphate sodium, fotemustine, Unimed G-6-M, Chinoin GYKI-17230, hepsulfam, ifosfamide, iproplatin, lomustine, mafosfamide, mitolactol, Nippon Kayaku NK-121, NCI NSC-264395, NCI NSC-342215, oxaliplatin, Upjohn PCNU, prednimustine, Proter PTfT-l9, ranimustine, semustine, SmithKline SK&F-101772, Yakult Honsha SN-22, spiromus-tine, Tanabe Seiyaku TA-077, tauromustine, temozolomide, teroxirone, tetraplatin and trimelamol.

A third family of antineoplastic agents which may be used in combination with a selective cyclooxygenase-2 inhibitor consists of antibiotic-type antineoplastic agents. Suitable antibiotic-type antineoplastic agents may be selected from the group consisting of Taiho 4181-A, aclarubicin, actinomycin D, actinoplanone, Erbamont ADR-456, aeroplysinin derivative, Ajinomoto AN-201-II. Ajinomoto AN-3, Nippon Soda anisomycins, anthracycline, azino-mycin-A, bisucaberin, Bristol-Myers BL-6859, Bristol-Myers BMY-25067. Bristol-Myers BMY-25551, Bristol-Myers BMY-26605, Bristol-Myers BMY-27557, Bristol-Myers BMY-28438, bleomycin sulfate, bryostatin-1, Taiho C-1027, calichemycin, chromoximycin, dactinomycin, daunorubicin, Kyowa Hakko DC-102, Kyowa Hakko DC-79, Kyowa Hakko DC-88A, Kyowa Hakko DC89-A1, Kyowa Hakko DC92-B, ditrisarubicin B, Shionogi DOB-41, doxorubicin, doxorubicin-fibrinogen, elsamicin-A, epirubicin, erbstatin, esorubicin, esperamicin-A1,esperamicin-Alb. Erbamont FCE-21954, Fujisawa FK-973, fostriecin, Fujisawa FR-900482, glidobactin, gregatin-A, grincamycin, herbimycin, idarubicin, illudins, kazusamycin, kesarirhodins, Kyowa Hakko KM-5539, Kirin Brewery KRN-8602, Kyowa Hakko KT-5432, Kyowa Hakko KT-5594, Kyowa Hakko KT-6149, American Cyanamid LL-D49194, Meiji Seika ME 2303, menogaril, mitomycin, mitoxantrone, SmithKline M-TAG, neoenactin, Nippon Kayaku NK-313, Nippon Kayaku NKT-Ol, SRI International NSC-357704, oxalysine, oxaunomycin, peplomycin, pilatin, pirarubicin, porothramycin, pyrindamycin A, Tobishi RA-I, rapamycin, rhizoxin, rodorubicin, sibanomicin, siwenmycin, Sumitomo SM-5887, Snow Brand SN-706, Snow Brand SN-07, sorangicin-A, sparsomycin, SS Pharmaceutical SS-21020, SS Pharmaceutical SS-7313B, SS Pharmaceutical SS-9816B, steffimycin B, Taiho 4181-2, talisomycin, Takeda TAN-868A, terpentecin, thrazine, tricrozarin A, Upjohn U-73975, Kyowa Hakko UCN-10028A, Fujisawa WF-3405, Yoshitomi Y-2S024 and zorubicin.

A fourth family of antineoplastic agents which may be used in combination with the selective cyclooxygenase-2 inhibitor consists of a miscellaneous family of antineoplastic agents selected from the group consisting of alpha-carotene, alpha-difluoromethyl-arginine, acitretin, Biotec AD-5, Kyorin AHC-52, alstonine, amonafide, amphethinile. amsacrine, Angiostat, ankinomycin, anti-neoplaston AIO, antineoplaston A2, antineoplaston A3, antineoplaston AS, antineoplaston AS2-1, Henkel APD, aphidicolin glycinate, asparaginase, Avarol, baccharin, batracylin, benfluron, benzotript, Ipsen-Beaufour BIM-23015, bisantrene, Bristo-Myers BMY-40481, Vestar boron-1O, bromofosfamide, Wellcome BW-502, Wellcome BW-773, caracemide, carme- thizole hydrochloride, Ajinomoto CDAF, chlorsulfaquinoxalone, Chemes CHX-2053, Chemex CHX-1OO, Warner-Lambert CI-921, Warner-Lambert CI-937, Warner-Lambert CI-941, Warner-Lambert CI-958, clanfenur, claviridenone, ICN compound 1259, ICN compound 4711, Contracan, Yakult Honsha CPT-11, crisnatol, curaderm, cytochalasin B, cytarabine, cytocytin, Merz D-609, DABIS maleate, dacarbazine, datelliptinium, didemnin-B, dihaematoporphyrin ether, dihydrolenperone, dinaline, distamycin, Toyo Phannar DM-341, Toyo Phaimar DM-75, Daiichi Seiyaku DN-9693, elliprabin, elliptinium acetate, Tsumura EPMTC, ergotamine, etoposide, etretinate, fenretinide, Fujisawa FR-57704, gallium nitrate, genkwadaphnin, Chugai GLA43, Glaxo GR-63178, grifolan NMF-5N, hexadecylphosphocholine, Green Cross HO-221, homoharringtonine, hydroxyurea, BTG ICRF-187, ilmofosine, isoglutamine, isotretinoin. Otsuka JI-36, Ramot K-477, Otsuak K-76COONa, Kureha Chemical K-AM, MEECT Corp KI-8110, American Cyanamid L-623, leukoregulin, lonidamine, Lundbeck LU-23-112, Lilly LY-186641, NCI (US) MAP, marycin, Merrel Dow MDL-27048, Medco MEDR-340, merbarone, merocyanine derivatives, methylanilinoacridine, Molecular Genetics MGI- 136, minactivin, mitonafide, mitoquidone, mopidamol, motretinide, Zenyaku Kogyo MST-16, N-(retinoyl)amino acids, Nisshin Flour Milling N-021, N-acylated-dehydroalanines, nafazatrom, Taisho NCU-190, nocodazole derivative, Normosang, NCI NSC-145813, NCI NSC-361456, NCI NSC-604782, NCI NSC-95580, octreotide, Ono 0N0-1 12, oquizanocine, Akzo Org10172, pancratistatin, pazelliptine, Warner-Lambert PD-111707, Wamner-Lambert PD-115934, Wamner-Lambert PD-131141, Pierre Fabre PE-1001, ICRT peptide D, piroxantrone, polyhaematoporphyrin, polypreic acid, Efamol porphyrin, probimane, procarbazine, proglumide, Invitron protease nexin 1, Tobishi RA-700, razoxane, Sapporo Breweries RBS, restrictinP, retelliptine, retinoic acid, Rhone-Poulenc RP-49532, Rhone-Poulenc RP-56976, Smithkline SK&F104864, Sumitomo SM-108, Kuraray SMANCS, SeaPharm SP-10094, spatol, spirocyclopropane derivatives, spirogermanium, Unimed, SS Pharmaceutical SS554, strypldinone, Stypoldione, Suntory SUN 0237, Suntory SUN 2071, superoxide dismutase, Toyama T-506, Toyama T-680, taxol, Teijin TEI-0303, teniposide, thaliblastine, Eastman Kodak TJB-29, tocotrienol, Topostin, Teijin TT-82, kyowa Hakko UCN-O1, Kyowa Hakko UCN-1028, ukrain, Eastman Kodak USB-006, vinbiastine sulfate, vincristine, vindesine, vinestrrnde, vinorelbine, vintriptol, vinzolidine, withaolides and Yamnanouchi YM-534.

Examples of radioprotective agents which may be used in the combination chemotherapy of this invention are AD-5, adchnon, amifostine analogues, detox, dimesna, 1-102, MN-159, N-acylated-dehydroalanines, TGF-Genentech, tiprotimod, amifostine, WR-151327, FUT-187, ketoprofen transdermal, naburnetone, superoxide dismutase (Chiron) and superoxide disrrtutase Enzon.

Methods for preparation of the antineoplastic agents described above may be found in the literature. Methods for preparation of doxorubicin, for example, are described in U.S. Pat. No. 3,590,028 and U.S. Pat. No 4,012,448. Methods for preparing metallomatrix protease inhibitors arc described in EP 780386, W097/20824. W096/15096. Methods for preparing SOD mimics are described in EP 524,101. Methods for preparing alpha,beta, inhibitors are described in W097/08174.

In addition, the selective COX-2 inhibitor may be administered in conjunction with other antiinflammatory agents for maximum safety and efficacy, including NSAID's, selective COX-1 inhibitors and inhibitors of the leukotriene pathway, including 5-lipoxygenase inhibitors. Examples of NSAID's include indomethacin, naproxen, ibruprofen, salicylic acid derivatives such as aspirin, diclofenac, ketorolac, piroxicam, meloxicam, mefenamic acid, sulindac, tolmetin sodium, zomepirac, fenoprofen, phenylbutazone, oxyphenbutazone, nimesulide, zaltoprofen and letodolac.

Method for assessing biological activities

The activity of the compounds of the formula (I) of the present invention was demonstrated by the following assays.

In vitro assays

Human cell based COX-1 assay

Human peripheral blood obtained from healthy volunteers was diluted to 1/10 volume with 3.8% sodium citrate solution. The platelet-rich plasma immediately obtained was washed with 0.14 M sodium chloride containing 12 mM Tris-HCl (pH 7.4) and 1.2 mM EDTA. Platelets were then washed with platelet buffer (Hanks buffer (Ca free) containing 0.2% BSA and 20 mM Hepes). Finally, the human washed platelets (HWP) were suspended in platelet buffer at the concentration of $2.85 \times 10^8$ cells/ml and stored at room temperature until use. The HWP suspension (70 μl aliquots, final $2.0 \times 10^7$ cells/ml) was placed in a 96well U bottom plate and 10 μl aliquots of 12.6 mM CaCl2 added. Platelets were incubated with A23187 (final 10 μM, Sigma) with test compound (0.1–100 μM) dissolved in DMSO (final concentration; less than 0.01%) at 37° C. for 15 min. The reaction was stopped by addition of EDTA (final 7.7 mM) and TxB2 in the supernatant quantitated by using a radioimmnunoassay kit (Amersham) according to the manufacturer's procedure.

Human cell based COX-2 assay

Inhibition of COX-2 activity after induction of COX-2 by hIL-1β

The human cell based COX-2 assay was carried out as previously described (Moore et al., *Inflam. Res.*, 45, 54, 1996). Confluent human umbilical vein endothelial cells (HUVECs, Morinaga) in a 96-well U bottom plate were washed with 100 μl of RPMI1640 containing 2% FCS and incubated with hIL-1β (final concentration 300 U/ml, R & D Systems) at 37° C. for 24 hr. After washing, the activated HUVECs were stimulated with A23187 (final concentration 30 μM) in Hanks buffer containing 0.2% BSA, 20 mM Hepes and test compound (0.1 nM–100 μM) dissolved in DMSO (final concentration; less than 0.01%) at 37 ° C. for 15 min. 6-Keto-PGF1α, stable metabolite of PGI2, in the supernatant was quantitated after adequate dilution by using a radioimmunoassay kit (Amersham) according to the manufacturer's procedure.

Inhibition of COX-2 during the induction phase

Confluent human umbilical vein endothelial cells (HUVECs, Morinaga) in a 96-well U bottom plate were washed with 100 μl of RPMI1640 containing 2% FCS and test compound (0.1 nM–100 μM) dissolved in DMSO (final concentration; less than 0.01%), and incubated with hIL-1β (final concentration 300 U/ml, R & D Systems) at 37° C. for 24 hr. After washing, the HUVECs were stimulated with A23187 (final concentration 30 μM) in Hanks buffer containing 0.2% BSA and 20 mM Hepes at 37° C. for 15 min. 6Keto-PGF1α, a stable metabolite of PGI2, in the supernatant was quantitated after adequate dilution by using a radioimmunoassay kit (Amersham) according to the manufacturer's procedure.

In vivo assays

Carrageenan induced foot edema in rats

Male Sprague-Dawley rats (5 weeks old, Charles River Japan) were fasted overnight. A line was drawn using a marker above the ankle on the right hind paw and the paw volume (V0) was measured by water displacement using a plethysmometer (Muromachi). Animals were given orally either vehicle (0.1% methyl cellulose or 5% Tween 80) or a test compound (2.5 ml per 100 g body weight). One hour later, the animals were then injected intradermally with λ-carrageenan (0.1 ml of 1% w/v suspension in saline, Zushikagaku) into right hind paw (Winter et al, *Proc. Soc. Exp. Biol. Med.*, 111, 544, 1962; Lombardino et al., *Arzneim. Forsch.*, 25, 1629, 1975) and three hours later, the paw volume (V3) was measured and the increase in volume (V3–V0) calculated Since maximum inhibition attainable with classical NSAIDs is 60–70%, ED30 values were calculated.

Gastric ulceration in rats

The gastric ulcerogenicity of test compound was assessed by a modification of the conventional method (Ezer et al., *J. Pharm. Pharmacol.*, 28, 655, 1976; Cashin et al., *J. Pharm. Pharmacol.*, 29, 330–336, 1977). Male Sprague-Dawley rats (5 weeks old, Charles River Japan), fasted overnight, were given orally either vehicle (0.1% methyl cellulose or 5% Tween 80) or a test compound (1 ml per 100 g body weight). Six hours after, the animals were sacrificed by cervical dislocation. The stomachs were removed and inflated with 1% formalin solution (10 ml). Stomachs were opened by cutting along the greater curvature. From the number of rats that showed at least one gastric ulcer or haemorrhaging erosion (including ecchymosis), the incidence of ulceration was calculated. Animals did not have access to either food or water during the experiment.

Data Analysis

Statistical program packages, SYSTAT (SYSTAT, INC.) and StatView (Abacus Cencepts, Inc.) for Macintosh were used. Differences between test compound treated group and control group were tested for using ANOVA. The $IC_{50}$ ($ED_{30}$) values were calculated from the equation for the log-linear regression line of concentration (dose) versus percent inhibition.

Some compounds prepared in the Working Examples as described herein after were tested by these methods, and showed $IC_{50}$ values of 0.001 μM to 10 μM with respect to inhibition of COX-2.

Also, the above-mentioned most preferred compounds were tested by these methods, and showed $IC_{50}$ values of 0.001 μM to 0.5 μM with respect to inhibition of COX-2.

COX-2 selectivity can be determined by ratio in terms of $IC_{50}$ value of COX-1 inhibition to COX-2 inhibition In general, it can be said that a compound showing a COX-1/COX-2 inhibition ratio of more than 2 has good COX-2 selectivity.

Some compounds prepared in Examples showed COX-1/COX-2 inhibition ratio of more than 10.

The following examples contain detailed descriptions of the methods of the preparation of compounds of formula (I). These detailed descriptions fall within the scope of the invention and serve to exemplify the above described general synthetic procedures which form part of the invention. These detailed descriptions are presented for illustrative purposes only and are not intended to restrict the scope of the present invention.

EXAMPLES

The invention is illustrated in the following non-limiting examples in which, unless stated otherwise: all operations were carried out at room or ambient temperature, that is, in the range of 18–25° C.; evaporation of solvent was carried out using a rotary evaporator under reduced pressure with a bath of up to 60° C.; reactions were monitored by thin layer chromatography (tlc) and reaction times are given for illustration only; melting points (mp) given are uncorrected (polymorphism may result in different melting points); structure and purity of all isolated compounds were assured by at least one of the following techniques: tlc (Merck silica gel 60 F precoated plates), mass spectrometry, nuclear magnetic resonance (NMR) or microanalysis. Yields are given for illustrative purpose only Flash column chromatography was carried out using Merck silica gel 60 (230–400 mesh ASTM). NMR data was determined at 270 MHz (JEOL GX 270 spectrometer) using deuterated chloroform (99.9% D) or dimethylsulfoxide (99.9% D) as solvent unless indicated otherwise, relative to tetramethylsilane (TMS) as internal standard in parts per million (ppm); conventional abbreviations used are: s=singlet, d=doublet, dd=double doublet, t=triplet, q=quartet, m=multiplet, and br=broad, etc.

Example 1

Methyl N-(2-Benzoyl-6-Chloro-1H-Indol-3-Yl) Carbamate

Step 1. 4-Chloro-2-[(ethoxycarbonyl)amino] benzonitrile

Method A:

To a solution of 2-amino4-chlorobenzonitrile (10.0 g, 65.5 mmol) in DMF (30 ml) cooled to 0° C. was added sodium hydride (60% w/w dispersion in mineral oil, 2.75 g, 68.7 mmol) portionwise over 10 min. The mixture was stirred for 1 h at 0° C. and then ethyl chloroformate (6.6 ml, 68.7 mmol) slowly added. After stirring for an additional hour at this temperature, the mixture was poured into water (300 ml) and extracted with diethyl ether (250 ml×2). The combined organic extracts were washed consecutively with water (500 ml), brine (500 ml), and then dried (MgSO$_4$). Removal of solvent gave 15.85 g (quant.) of the title compound as yellow solids.

Alternatively,

Method B:

To a suspension of 2-amino-4-chlorobenzonitrile (50 g, 0.33 mol) in a mixture of pyridine (40 ml, 0.50 mol) and dichloromethane (500 ml) cooled to 0° C., was carefully added ethyl chloroformate (35 ml, 0.37 mol). The mixture was allowed to warm to room temperature and stirred overnight. The mixture was poured into 2N aqueous HCl (300 ml) and extracted with dichloromethane (300 ml×2). Removal of solvent gave 75 g of crude product as pale yellow solids. The solid was washed with minimal hexane to afford 64 g (86%) of the title compound as white solids.

$^1$H-NMR (CDCl$_3$)δ 8.35 (1H, d, J=1.8 Hz), 7.47 (1H, d, J=8.4 Hz), 7.17 (1H, br s), 7.09 (1H, dd, J=8.4, 1.8 Hz), 4.28 (2H, q, J=7.0 Hz), 1.35 (3H, t, J=7.0 Hz)

Step 2. Ethyl 3-amino-2-benzoylchloro-1H-indole-1-caboxylate

To a solution of 4-chloro-2-[(ethoxycarbonyl)amino] benzonitrile (step 1, 10.8 g, 48 mmol) in DMF (50 ml) cooled to 0° C. was added sodium hydride (60% w/w dispersion in mineral oil, 2.0 g, 50 mmol). The mixture was stirred for 30 min at 0° C. and then 2-bromoacetophenone (9.9 g, 50 mmol) was carefully added. After stirring for an additional 15 h at 0° C., the mixture was poured into water (500 ml) and extracted with diethyl ether (500 ml×2). After drying (MgSO$_4$) and removal of solvent, the crude product was purified by flash chromatography eluting with ethyl acetate/hexane (1:5) to afford 11.8 g (72%) of the title compound as brown amorphous solids.

$^1$H-NMR (CDCl$_3$)δ 8.26 (1H, d, J=1.8 Hz), 7.78–7.70 (2H, m), 7.54 (1H, d, J=8.4 Hz), 7.50–7.39 (3H, m), 7.31 (1H, dd, J=1.8, 8.4 Hz), 5.78 (2H, br s), 3.73 (2H, q, J=7.0 Hz), 0.84 (3H, t, J=7.0 Hz).

Step 3. Ethyl 2-benzoyl-6chloro-3-[(methoxycarbonyl)amino]-1H-indole-1-caboxylate To a solution of ethyl 3-amino-2-benzoyl-6-chloro-1H-indole-1-caboxylate (step 2, 1.5 g, 4.4 mmol) and pyridine (0.50 ml, 6.6 mmol) in dichloromethane (20 ml) was added methyl chloroformate (0.40 ml, 5.3 mmol) at room temperature. After stirring for 3 h, the mixture was poured into 2N aqueous HCl (20 ml) and extracted with dichloromethane (30 ml×2). The combined organic layers were dried (MgSO$_4$) and concentrated to give 1.7 g (quant.) of the title compound as yellow amorphous solids.

$^1$H-NMR (CDCl$_3$)δ 8.52 (1H, br s), 8.27 (1H, d, J=1.8 Hz), 8.02 (1H, d, J=8.8 Hz), 7.80–7.73 (2H, m), 7.60–7.42 (3H, m), 7.32 (1H, dd, J=1.8, 8.8 Hz), 3.85 (2H, q, J=7.3 Hz), 3.78 (3H, s), 0.92 (3H, t, J=7.3 Hz).

Step 4. Methyl N-(2-benzoyl-6-chloro-1H-indol-3-yl)carbamate

To a stirred solution of ethyl 2-benzoyl-6-chloro-3-[(methoxycarbonyl)amino]-1H-indole-1-caboxylate (step 3, 680 mg, 1.7 mmol) in ethanol (20 ml) was added 2N aqueous KOH (10 ml) at room temperature. After stirring for 2 h, the mixture was concentrated and extracted with dichloromethane (50 ml×2). The combined organic layers were dried (MgSO$_4$) and concentrated to give an crystalline residue. Recrystallization from ethyl acetate/hexane afforded 320 mg (57%/o) of the title compound as yellow solids.

mp 186–190° C.

$^1$H-NMR (CDCl$_3$)δ 9.25 (1H, br s), 8.23 (1H, d, J=8.8 Hz), 8.21 (1H, br s), 7.82–7.77 (2H, m), 7.68–7.52 (3H, m), 7.29 (1H, d, J=1.8 Hz), 7.10 (1H, dd, J=1.8, 8.8 Hz), 3.81 (3H, s).

Example 2

Ethyl N-(2-Benzoyl-6-Chloro-1H-Indol-3-Yl) Carbamate

The title compound was prepared according to the procedure described in Example 1 except that ethyl chloroformate was used in place of methyl chloroformate.

mp 159–161° C.

IR (KBr) ν 1695, 1580, 1540, 1345, 1240, 1060, 920, 720 cm$^{-1}$ $^1$H-NMR (CDCl$_3$)δ 9.22 (1H, br s), 8.25 (1H, d, J=8.8 Hz), 8.16 (1H, br s), 7.82–7.75 (2H, m), 7.68–7.50 (3H, m), 7.28 (11H, d, J=1.8 Hz), 7.10 (1H, dd, J=8.8, 1.8 Hz), 4.25 (2H, q, J=7.3 Hz), 1.33 (3H, t, J=7.3 Hz).

Example 3

Ethyl N-[6-Chloro-2-(3-Methylbenzoyl)-1H-Indol-3-Yl]Carbamate

Step 1. Ethyl 3-amino-6chloro-2-(3-methylbenzoyl)-1H-indole-1-caboxylate

The title compound was prepared according to the procedure described in step 2 of Example 1 from 4-chloro-2-

[(ethoxycarbonyl)amino]benzonitrile (Example 1, step 1) and 2-bromo-3'-methylacetophenone (R. Yveline, G. Gerard, and M. Geroges, *Chem.Pharm.Bull.*, 1992,40, 1170.).

tlc: Rf=0.5 (25% ethyl acetate in hexanes)

Step 2. 3-Amino-6-chloro-2-(3-methylbenzoyl)-1H-indole

A mixture of ethyl 3-amino-6-chloro2-(3-methylbenzoyl)-1H-indole-1-caboxylate (step 1, 6.4 g, 18 mmol), $K_2CO_3$ (6.3 g, 45 mnmol), EtOH (50 ml) and water (30 ml) was heated at reflux temperature for 20 h. The mixture was concentrated, and then water (30 ml) was added to the residue. The resulting mixture was extracted with dichloromethane (80 ml×2) and the combined extracts were dried ($MgSO_4$). Removal of solvent gave 4.3 g (84%) of brown amorphous solids.

mp 80–88° C.

$^1$H-NMR ($CDCl_3$)δ 7.63 (1H, br s), 7.60–7.38 (5 H, m), 7.23 (1H, d, J=1.8 Hz), 7.02 (1H, dd, J=1.8, 8.8 Hz), 5.56(2H, br s), 2.45 (3H, s)

Step 3. Ethyl N-[6-chloro-2-(3-methylbenzoyl)-1H-indol-3-yl]carbamate

The title compound was prepared according to the procedure described in step 3 of Example 1 from 3-amino-6-chloro-2-(3-methylbenzoyl)-1H-indole (step 2) and ethyl chloroformate.

mp 154–157° C.

$^1$H-NMR ($CDCl_3$)δ 9.20 (1H, br s), 8.29 (1H, br s), 8.22 (1H, d, J=8.8 Hz), 7.61–7.53 (2H, m), 7.45–7.39 (2H, m), 7.28 (1H, d, J=1.8 Hz), 7.08 (1H, dd, J=8.8, 1.8 Hz), 4.24 (2H, q, J=7.0 Hz), 2.46 (3H, s), 1.33 (3H, t, J=7.0 Hz).

Example 4

Ethyl N-[6-Chloro-2-(3-Chlorobenzoyl)-1H-Indol-3-Yl]Carbamate

Step 1. Ethyl 3-amino-6-chloro-2-(3-chlorobenzoyl)-1H-indole-1-caboxylate

The title compound was prepared according to the procedure described in step 2 of Example 1 from 4-chloro-2-[(ethoxycarbonyl)amino]benzonitrile (Example 1, step 1) and 2-bromo-3'-chloroacetophenone (M. Kihara, M. Kashimoto, and Y. Kobayashi, *Tetrahedron*, 1992, 48, 67–78.).

$^1$H-NMR ($CDCl_3$) δ 8.25 (1H, d, J=1.5 Hz), 7.74 (1H, dd, J=1.5, 2.2 Hz), 7.58 (1H, dt, J=1.5, 7.7 Hz), 7.53 (1H, d, J=8.4 Hz), 7.47–7.43 (1H, m), 7.37 (1H, d, J=7.3 Hz), 7.32 (1H, dd, J=1.8, 8.4 Hz), 5.86 (2H, br s), 3.84 (2H, q, J=7.0 Hz), 0.93 (3H, t, J=7.0 Hz)

Step 2. 3-Amino-6-chloro-2-(3-chlorobenzoyl)-1H-indole

The title compound was prepared according to the procedure described in step 2 of Example 3 from ethyl 3-amino-6-chloro-2-(3-chlorobenzoyl)-1H-indole-1-caboxylate (step 1).

mp 99–102° C.

$^1$H-NMR ($CDCl_3$) δ 7.78 (1H, t, J=1.5 Hz), 7.68 (1H, ddd, J=1.5, 1.8, 7.3 Hz), 7.55–7.44 (4 H, m), 7.25 (1H, d, J=1.8 Hz), 7.04 (1H, dd, J=1.8, 8.8 Hz), 5.68 (2H, br s).

Step 3. Ethyl N-[6-chloro-2-(3-chlorobenzoyl)1H-indol-3-yl]carbamate

The title compound was prepared according to the procedure described in step 3 of Example 1 from 3-amino-6-chloro-2-(3-chlorobenzoyl)-1H-indole (step 2) and ethyl chloroformate.

mp 188–189° C.

$^1$H-NMR ($CDCl_3$)δ 9.08 (1H, br s), 8.24 (1H, d, J=8.8 Hz), 8.16 (1H, br s), 7.78 (1H, t, J=1.8 Hz), 7.70–7.57 (2H, m), 7.50 (1H, t, J=7.7 Hz), 7.32 (1H, d, J=1.8 Hz), 7.12 (1H, dd, J=1.8 and 9.2 Hz), 4.25 (21H, q, J=7.0 Hz), 1.33 (3H, t, J=7.0 Hz).

Example 5

N-(2-Benzoyl-6-Chloro-1H-Indol-3-Yl)Urea

Step 1. 3-Amino-2-benzoyl-6-chloroindole

The title compound was prepared according to the procedure described in step 2 of Example 3 from ethyl 3-amino-2-benzoyl-6-chloro-1H-indole-1-carboxylate (Example 1, step 2).

mp 128–130° C.

$^1$H-NMR ($CDCl_3$)δ 7.85–7.76 (2H, m), 7.64 (1H, br s), 7.59–7.49 (4 H, m), 7.22 (1H, d, J=1.8 Hz), 7.02 (1H, dd, J=1.8, 8.4 Hz), 5.60 (2H, br s).

Step 2. N-(2-Benzoyl-6-chloro-1H-indol-3-yl)urea

To a solution of 3-amino-2-benzoyl-6-chloroindole (step 1, 60 mg, 0.21 mmol) in acetic acid (10 ml) was added sodium cyanate (14 mg, 0.21 mmol) and the mixture was stirred for 1.5 h at 90° C. After cooling, the mixture was poured into a saturated sodium bicarbonate (50 ml) and extracted with ethyl acetate (40 ml×2), dried ($MgSO_4$) and concentrated. The residual solids were purified by flash column chromatography eluting with hexane/ethyl acetate (1/1) to give 10 mg (15%) of the title compound as yellow solids.

mp 196–200° C.

IR(KBr)ν 1660, 1620, 1570, 1540, 1500, 1320, 1230, 920 $cm^{-1}$ $^1$H-NMR ($CDCl_3$)δ 9.12 (1H, br s), 8.22 (1H, m), 7.88–7.50 (6 H, m), 7.40–7.28 (2H, m), 5.38 (2H, br s).

Example 6

N-[6-Chloro-2-(3-Methylbenzoyl)-1H-Indol-3-Yl]Urea

The title compound was prepared according to the procedure described in step 2 of Example 5 from 3-amino-6-chloro-2-(3-methylbenzoyl)-1H-indole (Example 3, step 2).

mp>280° C.

$^1$H-NMR ($CDCl_3$)δ 9.84 (11H, br s), 8.96 (1H, s), 8.06 (1H, d, J=8.8 Hz), 7.69–7.61 (2H, m), 7.45–7.36 (3H, m), 7.04 (1H, dd, J=8.8, 1.8 Hz), 5.29 (2H, br s), 2.58 (3H, s).

Example 7

N-(2-Benzoyl-6-Chloro-1H-Indol-3-Yl)-N'-Ethylurea

To a solution of ethyl 3-amino-2-benzoyl-6-chloro-1H-indole-1-carboxylate (step 2 of Example 1, 500 mg, 1.46 mmol) in dichloromethane (20 ml) and pyridine (1.0 ml) was added phenyl chloroformate (250 mg, 1.6 mmol) and the mixture was stirred for 1h at room temperature. The mixture was pored into 2N aqueous HCl (10 ml) and extracted with dichloromethane (30 ml×2), dried ($MgSO_4$) and concentrated to afford 650 mg of yellow amorphous solids. These solids were dissolved in pyridine (20 ml), and then ethylamine (70% in water, 0.56 ml, 7.0 mmol) was added. After stirring for 30 min at room temperature, the mixture was poured into water (30 ml) and extracted with dichloromethane (30 ml×2). The organic extracts were washed with 2N aqueous HCl (50 ml), brine (50 ml), dried (MgSO$_4$), and concentrated. The residual solids were purified by flash column chromatography eluting with hexane/ethyl acetate (3/2) to give yellow solids. Recrystallization from ethyl acetate/hexane gave 160 mg (33%) of the title compound as yellow solids.

mp 222–235° C.

IR(KBr)v 1620, 1570, 1540, 1450, 1320, 1255, 1230 cm$^{-1}$ $^1$H-NMR (CDCl$_3$)δ 9.33 (1H, br s), 8.27 (1H, d, J=8.8 Hz), 8.19 (1H, br s), 7.83–7.73 (2H, m), 7.67–7.52 (3H, m), 7.24 (1H, d, J=1.8 Hz), 7.07 (1H, dd, J=8.8, 1.8 Hz), 4.93 (1H, br s), 3.42–3.26 (2H, m), 1.20 (3H, t, J=7.3 Hz).

Example 8

N-(2-Benzoyl-6-Chloro-1H-Indol-3-Yl)-N'-Methylurea

The title compound was prepared according to the procedure described in Example 7 except that methylamine (40% in water) was used in place of ethylamine.

mp 270–275° C.

IR(KBr)v 1660, 1620, 1570, 1540, 1500, 1320, 1230,920 cm$^{-1}$ $^1$H-NMR (CDCl$_3$)δ 10.28 (11H, br s), 9.28 (1H, br s), 8.20–8.10 (11H, m), 7.91–7.80 (2H, m), 7.67–7.48 (3H, m), 7.43–7.33 (1H, m), 7.04–6.95 (1H, m), 6.13 (1H, br s), 2.85 (3H, s).

Example 9

N-(2-Benzoyl-6-Chloro-1H-Indol-3-Yl)N'-Propylurea

The title compound was prepared according to the procedure described in Example 7 except that propylamine was used in place of ethylamine.

mp 234–236° C.

IR(KBr)v 1630, 1565, 1450, 1320, 1255, 1230 cm$^{-1}$ $^1$H-NMR (CDCl$_3$)δ 9.68 (1H, br s), 9.23 (1H, br s), 8.16 (1H, d, J=8.8 Hz), 7.88–7.79 (2H, m), 7.64–7.48 (3H, m), 7.32 (1H, d, J=1.8 Hz), 7.01 (1H, dd, J=8.8, 1.8 Hz), 5.66 (1H, br s), 3.30–3.15 (2H, m), 1.68–1.50 (2H, m), 0.94 (3H, t, J=7.3 Hz).

Example 10

N-(2-Benzoyl-6-Chloro-1H-Indol-3-Yl)-N'-Isobutylurea

The title compound was prepared according to the procedure described in Example 7 except that isobutylarnine was used in place of ethylamine.

mp 235–238° C.

IR(KBr)v 1630, 1560, 1320, 1255, 1230, 1060, 980, 930 cm$^{31\ 1}$ $^1$H-NMR (CDCl$_3$) 5 10.02 (1H, br s), 9.23 (11H, br s), 8.28–8.10 (1H, m), 7.92–7.87 (2H, m), 7.70–7.47 (3H, m), 7.35 (11H, s), 7.10–6.94 (11H, m), 6.02 (1H, br s), 3.20–3.00 (2H, m), 1.91–1.71 (1H, m), 0.95 (6 H, d, J=6.6 Hz).

Example 11

N-(2-Benzoyl-6-Chloro-1H-Indol-3-Yl)-N'-(2-Methoxyethyl)Urea

The title compound was prepared according to the procedure described in Example 7 except that 2-methoxyethylamnine was used in place of ethylamine.

mp 208–212° C.

IR(KBr)v 1630, 1565, 1450, 1320, 1250, 1100, 985 cm$^{-1}$ $^1$H-NMR (CDCl$_3$)δ 9.29 (1H, br s), 8.25 (1H, d, J=8.8 Hz), 8.16 (1H, br s), 7.81–7.75 (2H, m), 7.64–7.51 (3H, m), 7.26 (11H, s), 7.08 (11H, dd, J=8.8, 1.8 Hz), 5.29 (1H, br s), 3.59–3.46 (4 H, m), 3.38 (3H, s).

Example 12

N-(2-Benzoyl-6-Chloro-1H-Indol-3-Yl)4-Morpholinecarboxamide

The title compound was prepared according to the procedure described in Example 7 except that morpholine was used in place of ethylamine.

mp 168–170° C.

IR (KBr) v 1630, 1580, 1540, 1480, 1320, 1250, 1120 cmu$^1$ $^1$H-NMR (CDCl$_3$)δ 10.27 (1H, br s), 8.37 (1H, d, J=8.8 Hz), 8.06 (1H, br s), 7.82–7.75 (2H, m), 7.70–7.52 (3H, m), 7.28 (1H, d, J=1.8 Hz), 7.09 (1H, dd, J=8.8, 1.8 Hz), 3.82–3.75 (4 H, m), 3.68–3.58 (4 H, m).

Example 13

N'-[6-Chloro-2-(3-Chlorobenzoyl)-1H-Indol-3-Yl]-N,N-Dimethylurea

The title compound was prepared according to the procedure described in Example 7 from ethyl 3-amino-6-chloro-2-(3-chlorobenzoyl)-1H-indole-1-carboxylate (Example 4, step 1) and dimethylamine mp214-21° C.

$^1$H-NMR (CDCl$_3$)δ 10.02 (1H, br s), 8.37 (1H, d, J=8.8 Hz), 8.05 (1H, br s), 7.78 (1 H, t, J=1.8 Hz), 7.68 (1H, dt, J=1.5, 1.5, 7.3 Hz), 7.59 (1H, ddd, J=1.5, 1.8, 8.1Hz), 7.47 (1H, t, J=7.7 Hz), 7.24 (1H, d, J=1.8 Hz), 7.06 (1H, dd, J=1.8, 9.2 Hz), 3.14 (6 H, s).

Example 14

N'-[6-Chloro-2-(3-Chlorobenzoyl)-1H-Indol-3-Yl]-N-Hydroxy-N-Methylurea

The title compound was prepared according to the procedure described in Example 7 from ethyl 3-amino-6chloro-2-(3-chlorobenzoyl)-1H-indole-1-carboxylate (Example 4, step 1) and N-methylhydroxylanine hydrochloride.

mp 205–206° C.

$^1$H-NMR (CDCl$_3$+3 drops of DMSO-d$_6$)δ 10.47 (2H, br s), 9.63 (1H, s), 8.35 (1H, d, J=8.4 Hz), 7.81 (1H br s), 7.73 (1H, d, J=7.3 Hz), 7.56 (1H, d, J=8.1Hz), 7.48 (1H, t, J=7.7 Hz), 7.00 (1H, dd, J=1.5, 7.7 Hz), 3 27 (3H, s).

Example 15

N-(2-Benzoyl-6-Chloro- 1H-Indol-3-Yl)-N'-Isopropylurea

To a solution of ethyl 3-amino-2-benzoyl-6-chloro-1H-indole-1-carboxylate (step2 of Example 3, 500 mg, 1.4 mmol) in dichloromethane (20 ml) and pyridine (1.0 ml) was added phenyl chloroformate (250 mg, 1.6 mmol) and the mixture was stirred for 1 h at room temperature. The mixture was poured into 2N aqueous HCl (10 ml) and extracted with dichloromethane (30 ml×2). The extracts were dried (MgSO$_4$) and concentrated to afford 550 mg of yellow amorphous solids. These solids were dissolved in pyridine (20 ml), and then isopropylamine (0.5 ml, 5.9 mmol) was added at room temperature. After stirring for 1h, the mixture was poured into 2N aqueous HCl (50 ml) and extracted with dichloromethane (30 ml×2). The combined extracts were dried (MgSO$_4$) and concentrated. The resulting amorphous solids were dissolved in EtOH, and 2N aqueous KOH (5 ml) was added at room temperature. After stirring for 1 h, the mixture was concentrated and extracted with ethyl acetate (50 5 ml×2). The combined organic extracts were dried (MgSO$_4$) and concentrated. The residual yellow amorphous solids were purified by flash column chromatography eluting with hexanelethyl acetate (2/1) to give yellow solids. Recrystallization from ethyl acetate/hexane gave 210 mg (50%) of the title compound as yellow solids.

mp 265–266° C.

IR(KBr)v 1620, 1560, 1325, 1255, 1225, 990, 920 cm$^{-1}$ $^1$H-NMR (DMSO-d$_6$)δ 11.34 (1H, br s), 8.82 (1H, br s), 7.90 (1H, d, J=8.8 Hz), 7.84–7.76 (2H, m), 7.68–7.52 (3H, m), 7.39 (1H, d, J=1.8 Hz), 7.03 (11H, dd, J=8.8, 1.8 Hz), 6.77 (1H, d, J=7.3 Hz), 3.80–3.62 (1H, m), 1.03 (6 H, d, J=6.6 Hz).

Example 16

N'-(2-Benzoyl-6-Chloro-1H-Indol-3-Yl)-N,N-Dimethylurea

The title compound was prepared according to the procedure described in Example 15 except that dimethylamine hydrochloride was used in place of isopropylamine.

mp 222–223° C.

IR(KBr)v 1660, 1580, 1540, 1500, 1360, 1320, 1260, 1020, 920 cm$^{-1}$ $^1$H-NMR (CDCl$_3$)δ 10.09 (1H, br s), 8.40 (1H, d, J=8.8 Hz), 8.01 (1H, br s), 7.86–7.77 (2H, m), 7.68–7.52 (3H, m), 7.25 (1H, d, J=1. Hz), 7.06 (1H, dd, 8.8, 1.8 Hz), 3.14 (6 H, s).

Example 17

N'-(2-Benzoyl-6-Chloro-1H-Indol-3-Yl)-N,N-Diethylurea

The title compound was prepared according to the procedure described in Example 15 except that diethylamine was used in place of isopropylamine.

mp 196–198° C.

IR(KBr)v 1640, 1580, 1480, 1340, 1260, 1020 cm$^{-1}$ $^1$H-NMR (CDCl$_3$)δ 10.11 (1H, br s), 8.40 (1H, d, J=8.8 Hz), 8.00 (1H, br s), 7.81–7.74 (2H, m), 7.66–7.52 (3H, m), 7.23 (1H, d, J=1.8 Hz), 7.06 (1H, dd, 8.8, 1.8 Hz), 3.50 (4 H, q, J=7.3 Hz), 3.14 (6 H, t, J=7.3 Hz).

Example 18

N'-(2-Benzoyl-6-Chloro-1H-Indol-3-Yl)N-Ethyl-N-Methylurea

The title compound was prepared according to the procedure described in Example 15 except that N-ethylmethylarnine was used in place of isopropylamine.

mp 159–161° C.

IR (KBr) v 1650, 1620, 1580, 1540, 1480, 1320, 1255, 1020 cm$^{-1}$ $^1$H-NMR (CDCl$_3$)δ 10.08 (1H, br s), 8.39 (1H, d, J=8.8 Hz), 8.05 (1H, br s), 7.85–7.78 (2H, m), 7.67–7.52 (3H, m), 7.23 (1H, d, J=1.8 Hz), 7.05 (1H, dd, J=8.8, 1.8 Hz), 3.51 (4 H, q, J=7.0 Hz), 3.12 (3H, s), 1.28 (3H, t, J=7.0 Hz).

Example 19

N'-(2-Benzoyl-6-Chloro-1H-Indol-3-Yl)-N-Methyl-N-Propylurea

The title compound was prepared according to the procedure described in Example 15 except that N-methylpropylamine was used in place of isopropylamine.

mp 168–171° C.

IR (KBr) v 1650, 1620, 1580, 1540, 1480, 1320, 1255, 1020 cm$^{-1}$ $^1$H-NMR (CDCl$_3$)δ 10.08 (1H, br s), 8.38 (1H, d, J=8.8 Hz), 8.06 (1H, br s), 7.85–7.75 (2H, m), 7.66–7.49 (3H, m), 7.23 (1H, d, J=1.8 Hz), 7.05 (1H, dd, J=8.8, 1.8 Hz), 3.42 (2H, t, J=7. Hz), 3.13 (3H, s), 1.82–1.68 (2H, m), 1.02 (3H, t, J=7.3 Hz).

Example 20

N'-(2-Benzoyl-6-Chloro-1H-Indol-3-Yl)-N-(2-Methoxyethyl)-N-Methylurea

The title compound was prepared according to the procedure described in Example 15 except that N-(2-methoxyethyl)methylamine was used in place of sopropylamine.

mp 66–72° C.

IR (KBr) v 1650, 1580, 1535, 1480, 1340, 1255, 1120, 1010, 920 cm$^{-1}$ $^1$H-NMR (CDCl$_3$)δ 9.91 (1H, br s), 8.25 (1H, d, J=8.8 Hz), 8.10 (1H, br s), 7.86–7.77 (2H, m), 7.67–7.50 (3H, m), 7.24 (1H, d, J=1.8 Hz), 7.05 (1H, dd, 8.8, 1.8 Hz), 3.62 (4 H, s), 3.41 (3H, s), 3.17 (3H, s).

Example 21

N-(2-Benzoyl-6-Chloro-1H-Indol-3-Yl)-4-Methyl-1-Piperazinecarboxamide

The title compound was prepared according to the procedure described in Example 15 except that 1-methylpiperazine dihydrochloride was used in place of isopropylamine.

mp 168–170° C.

IR (KBr) v 1630, 1580, 1540, 1480, 1320, 1260 cm$^{-1}$ $^1$H-NMR (CDCl$_3$)δ 10.22 (1H, br s), 8.36 (1H, d, J=8.8 Hz), 8.09 (1H, br s), 7.82–7.73 (2H, m), 7.68–7.50 (3H, m), 7.24 (1H, d, J=1.8 Hz), 7.06 (1H, dd, 8.8, 1.8 Hz), 3.70–3.60 (4 H, m), 2.52–2.42 (4 H, m), 2.35 (3H, s).

Example 22

N'-(2-Benzoyl-6-Chloro-1H-Indol-3-Yl)N-Hydroxy-N-Methylurea

The title compound was prepared according to the procedure described in Example 15 except that N-methylhydroxylamine hydrochloride was used in place of isopropylamine.

mp 208–214° C.

IR (KBr) v 1610, 1565, 1500, 1460, 1330, 1225, 1170, 920 cm$^{-1}$ $^1$H-NMR (CDCl$_3$)δ 10.51 (1H, br s), 9.34 (1H, br s), 9.21 (1H, s), 8.37 (1H, d, J=8.8 Hz), 7.88–7.80 (2H, m), 7.65–7.50 (3H, m), 7.33 (1H, d, J=1.8 Hz), 7.04 (1H, dd, J=8.8, 1.8 Hz),3.28 (3H, s).

Example 23

N'-(2-Benzoyl-6-Chloro-1H-Indol-3-Yl)-N-Methoxy-N-Methylurea

The title compound was prepared according to the procedure described in Example 15 except that N,O- dimethylhydroxylamine hydrochloride was used in place of isopropylamine.

mp 180–182° C.

$^1$H-NMR (CDCl$_3$)δ 10.46 (1H, br s), 8.39 (1H, d, J=8.8 Hz), 8.16 (1H, br s), 7.84–7.77 (2H, m), 7.68–7.52 (3H, m), 7.28 (1H, d, J=1.8 Hz), 7.09 (1H, dd, J=8.8, 1.8 Hz), 3.86 (3H, s), 3.24 (3H, s).

Example 24

N'-[6-Chloro-2-(3-Methylbenzoyl)-1H-Indol-3-Yl]-N,N-Dimethylurea

The title compound was prepared according to the procedure described in Example 15 from ethyl 3-amino-6-chloro2-(3-methylbenzoyl)-1H-indole-1-carboxylate (Example 3, step 1) and dimethylamine.

mp 198–200° C.

$^1$H-NMR (CDCl$_3$)δ 10.05 (1H, br s), 8.36 (1H, d, J=8.8 Hz), 8.14 (1H, br s), 7.62 –7.53 (2H, m), 7.46–7.38 (2H, m), 7.22 (1H, d, J=1.8 Hz), 7.04 1H, (dd, J=8.8, 1.8 Hz), 3.12 (6 H, s), 2.45 (3H, s).

Example 25

N'-[6-Chloro-2-(3-Methylbenzoyl)-1H-Indol-3-Yl]-N-Hydroxy-N-Methylurea

The title compound was prepared according to the procedure described in Example 15 from ethyl 3-amino-6-chloro-2-(3-methylbenzoyl)-1H-indole-1-carboxylate (Example 3, step 1) and N-methylhydroxylamine hydrochloride.

mp212–215° C.

$^1$H-NMR (DMSO-d$_6$)δ 10.50 (1H, br s), 9.78 (1H, br s), 9.43 (1H, br s), 8.36 (1H, d, J=8.8 Hz), 7.70–7.60 (2H, m), 7.50-7.30 (3H, m), 7.02 (1H, dd, J=8.8, 1.8 Hz), 3.27 (3H, s), 2.45 (3H, s).

Example 26

N'-[6-Chloro-2-(Cyclohexylcarbonyl)-1H-Indol-3-Yl]-N-Methoxy-N-Methylurea

Step 1 .Ethyl 3-amino-6-chloro-2-(cyclohexylcarbonoyl)- 1H-indole- 1-carboxylate The title compound was prepared according to the procedure described in step 2 of Example 1 from 4-chloro-2-[(ethoxycarbonyl)amino]benzonitrile (Example 1, step 1) and 2-bromoacetylcyclohexane (Lotfield, Schaad, *J. Am. Chem. Soc.,* 1954, 76, 35).

$^1$H-NMR (CDCl$_3$)δ 8.14 (1H, d, J=1.8 Hz), 7.45 (1H, d, J=8.4 Hz), 7.26 (1H, dd, J=1.8, 8.4 Hz), 5.66 (2H, br), 4.44 (2H, q, J=7.0 Hz), 2.95–2.72 (1H, m), 2.00–1.10 (13H, m)

STEP 2. N'-[6-Chloro-2-(cyclohexylcarbonyl)-1H-indol-3-yl]-N-methoxy-N-methylurea The title compound was prepared according to the procedure described in Example 15 from ethyl 3-amino-6-chloro-2-(cyclohexylcarbonyl)-1H-indole-1-carboxylate and N,O-dimethylhydroxylamine hydrochloride.

mp 208–210° C.

IR(KBr) v 3238,2928, 1657, 1645,1582,1547,1491, 1350cm$^{-1}$ $^1$H-NMR (CDCl$_3$)δ 10.17 (1H, br s), 8.51 (1H, br s), 8.23 (1H, d, J=8.9 Hz), 7.25 (1 H, dd, J=0.7, 1.8 Hz), 7.03 (1H, dd, J=1.8, 8.9 Hz), 3.89 (3 H, s), 3.25 (3 H, s), 2.93 (1 H, tt, J=3.1, 11.5 Hz), 1.93–1.24 (10 H, m).

Example 27

N'-[6-Chloro-2-(3-Hydroxymethyl-2-Furoyl)-1H-Indol-3-Yl]-N-Methoxy-N-Methylurea

Step 1. 3-Acetoxymethyl-2-(romoacetyl)furan

3-Acetoxymethyl-2-acetylfuran (1.7 g, 9.3 mmol, prepared according to the procedure described in Acta. Chemica. Scandinavia, 1990, 44, 916) was dissolved in acetic acid (30 ml). To the solution was added pyridinium tribromide (3.3 g, 10.2 mmol) and the resulting mixture was stirred at room temperature for 3 h. The mixture was cooled to 0° C. and made basic with saturated aqueous sodium bicarbonate. The mixture was extracted with ethyl acetate (100 ml). The organic extract was washed with brine (100 ml), dried (MgSO$_4$) and concentrated to give 2.3g (95%) of the title compound.

$^1$H-NMR (CDCl$_3$)δ 7.54 (1H, d, J=1.6Hz), 6.65 (1H, d, J=1.6 Hz), 5.38 (2H, s), 4.37 (2H, s), 2.09 (3H, s).

Step 2. Ethyl 2-[3-(acetoxymethyl)-2-furoyl]-3-amino6-chloro-1H-indole-1-carboxylate The title compound was prepared according to the procedure described in step 2 of Example 1 from 4-chloro-2-[(ethoxycarbonyl)amino]benzonitrile (Example 1, step 1) and 3-acetoxymethyl-2-(bromoacetyl)furan (Step 1).

$^1$H-NMR (CDCl$_3$)δ 8.27 (1H, d, J=1.3 Hz), 7.51 (1H, dd, J=8.2 Hz), 7.43 (1H, d, J=1.6 Hz), 7.27 (1H, dd, J=2.0, 8.4 Hz), 6.60 (1H, d, J=1.6 Hz), 5.50 (2H, s), 4.03 (2H, q, J=7.1Hz), 2.14 (3H, s), 1.03 (3H, t, J=7.1Hz). A signal due to NH was not observed.

Step 3. N'-[6-Chloro-2-(3-hydroxymethyl-2-furoyl)-1H-indol-3-yl]-N-methoxy-N-methylurea The title compound was prepared according to the procedure described in Example 15 (Step 2) from ethyl 2-[3-(acetoxymethyl)-2-furoyl]-3-amino-6-chloro-1H-indole-1-carboxylate and N,O-dimethylhydroxylamine hydrochloride.

mp 221–222° C.

IR (KBr) v 3329, 1663, 1576, 1545, 1491, 1475, 1412, 1352, 1263, 1056, 999, 972, 897, 775 cm$^{-1}$ $^1$H-NMR (CDCl$_3$)δ 11.22 (1H, br s), 9.40 (1H, br s), 8.57 (1H, d, J=8.6 Hz), 7.69 (1 H, d, J=1.3 Hz), 7.36 (1H, d, 3=1.5 Hz), 7.07 (1H, dd, J=2.0 and 8.9 Hz), 6.66 (1H, d, J=1.5 Hz), 4.81 (2H, s), 3.92 (3 H, s), 3.28 (3 H, s). One signal due to OH group was not observed.

Example 28

N'-[6-Chloro-2-(3-Hydroxymethyl-2-Furoyl)-1H-Indol-3-Yl]-N,N-Dimethylurea

The title compound was prepared according to the procedure described in Example 15 from ethyl 2-[3-(acetoxymethyl)-2-furoyl]-3-amino6-chloro-1H-indole-1-carboxylate (Example 27, step 2) and dimethylamine.

mp 238° C. (decompose)

IR (KBr) v 3335, 3126, 2937, 1645, 1618, 1557, 1564, 1543, 1483, 1414, 1344, 1259, 1190, 1059,991 cm$^{-1}$ $^1$H-NMR (DMSO-d$_6$)δ 11.36 (1H, br s), 10.06 (1H, br s), 8.19 (1H, d, J=8.9 Hz), 8.02 (1H, d, J=1.8 Hz), 7.55 (1H, d,

J=1.6 Hz), 7.01 (1H, dd, J=1.8 Hz and 8.9 Hz), 6.89 (1H, d, J=1.8 Hz), 5.30 (1H, br s), 4.81 (2H, br s), 3.02 (6H, s).

Example 29

N'-[6-Chloro-2-[(4-Methyl-2-Pyridinyl)Carbonyl]-1H-Indol-3-Yl]-N-Methoxy-N-Methylurea Step 1. Ethyl 3-amino-6-chloro-2-[(4methyl-2-pyridinyl)carbonyl]-1H-indole-1-carboxylate The title compound was prepared according to the procedure described in step 2 of Example 1 from 4-chloro-2-[(ethoxycarbonyl)amino]benzonitrile (Example 1, step 5 1) and 2-bromoacetyl4-methylpyridine hydrobromide (F. H. Case et al., J. Am. Chem. Soc., 1956, 78, 5842).

$^1$H-NMR (CDCl$_3$)δ 8.46 (1H, d, J=4.8 Hz), 8.22 (1H, d, J=1.8 Hz), 7.89 (1H, s), 7.51 (1H, d, J=8.4 Hz), 7.24(1H, dd, J=1.8, 8.4 Hz), 7.20 (1H, br d, J=4.8 Hz), 5.97(2H, br s), 3.80 (2H, q, J=7.0 Hz), 2.46 (3H, s), 0.90 (3H, t, J=7.0 Hz)

Step 2. 3-Amino-6-chloro-2-[(4-methyl-2-pyridinyl)carbonyl]-1H-indole

The tide compound was prepared according to the procedure described in step 2 of Example 3 from ethyl 3-amino-6-chloro-2-[(4-methyl-2-pyridinyl)carbonyl]-1H-indole-1-carboxylate (step 1).

mp 195–196° C.

$^1$H-NMR (DMSO-d$_6$)δ 11.11 (1H, br s), 8.59 (1H, d, J=5.1Hz), 8.17 (1H, s), 7.52 (1H, d, J=8.8 Hz), 7.33 (1H, d, J=1.5 Hz), 7.29 (1H , d, J=4.8 Hz), 6.96 (1H, dd, J=1.8, 8.4 Hz), 6.03 (2H, br s), 2.48 (3H, s).

Step 3. N'-[6-Chloro2-[(4-methyl-2-pyridinyl)carbonyl]-1H-indol-3-yl]-N-methoxy-N-methylurea To a solution of 3-amino-6-chloro2-[(4-methyl-2-pyridinylicarbonyl]-1H-indole (step 2, 400 mg, 1.40 mmol) in dichloromethane (40 ml) was added pyridine (0.55 ml) and phenyl chloroformate (0.26 ml, 2.10 mmol) at room temperature. After stirring for 0.5 h, MeOH (1 ml) was added and then the resulting mixture was concentrated. The residue was diluted with ethyl acetate (200 ml) and washed with 2N HCl (50 ml×2), saturated sodium bicarbonate (50 ml), and dried (MgSO$_4$). The organic layer was concentrated to give 726 mg of crystalline residue. The residue was dissolved in pyridine (10 ml) and then N,O-dimethylhydroxylamine hydrochloride (571 mg, 7.01 mmol) was added at room temperature. The mixture was heated at 110° C. for 6 h and concentrated. The residue was diluted with ethyl acetate (200 ml), washed with water (30 ml×3), and dried (MgSO$_4$). After removal of solvent, the residual solids were recrystallized from ethyl acetate to give 303 mg (58%) of the title compound as yellow solids.

mp 199–200° C.

IR (KBr) v 3271, 1699, 1614, 1591, 1574, 1545, 1487, 1350, 1205 cm$^{-1}$ $^1$H-NMR (CDCl$_3$)δ 11.93 (1H, br s), 11.31 (1H, br s), 8.62 (1H, d, J=4.9 Hz), 8.57 (1 H, d, J=9.2 Hz), 8.21 (1H, t, J=0.8 Hz), 7.39 (1H, dd, J=0.5 and 1.8 Hz), 7.35 (1H, m), 7.03 (1H, dd, J=1.8 and 9.1Hz), 3.96 (3 H, s), 3.28 (3 H, s), 2.49 (3 H, s).

Example 30

N'-[6-Chloro-2-[(4-Chloro-2-Pyridinyl)Carbonyl]-1H-Indol-3-Yl]-N-Methoxy-N-Methylurea Step 1. Ethyl 3-amino-6-chloro-2-[(4-chloro-2-pyridinyl)carbonyl]-1H-indole-1-carboxylate The title compound was prepared according to the procedure described in step 2 of Example 1 from 4-chloro-2-[(ethoxycarbonyl)amino]benzonitrile (Example 1, step 1) and 2-(bromoacetyl)4-chloropyridine hydrobromide*.

$^1$H-NMR (CDCl$_3$)δ 8.50 (1H, d, J=5.5 Hz), 8.20 (1H, d, J=1.8 Hz), 8.06 (1H, d, J=2.6 Hz), 7.52 (1H, d, J=8.4 Hz), 7.38 (1H, dd, J=1.8, 5.1Hz), 7.25 (1H, dd, J=1.8, 8.4 Hz), 6.06 (2H, br s), 3.86 (2H, q, J=7.0 Hz), 0.96 (3H, t, J=7.0 Hz)

* 2-(Bromoacetyl)4-chloropyridine hydrobromide was prepared as follows; 4-Chloro-2-pyridinecarbonitrile: To a mixture of 4-chloropiridine-N-oxide (5.00 g, 38.6 mmol) and trimethylsilyl cycanide (4.84 g, 46.3 mmol) in dichloromethane (60 ml) cooled to 0° C. was added dropwise N,N-dimethylcarbamoyl chloride (3.8 ml, 40.5 mmol). The mixture was allowed to warm to ambient temperature and stirred for 16 h. The mixture was cooled to 0° C. and a 30% aqueous solution of K$_2$CO$_3$ (100 ml) was added. The crude product was extracted with dichloromethane (100 ml×2), the organic extracts dried (MgSO$_4$) and evaporated to give 4-chloro-2-pyridinecarbonitrile (5.35 g, 100%).

$^1$H-NMR (CDCl$_3$)δ 8.63 (1H, d, J=4.8 Hz), 7.72 (1H, d, J=2.6 Hz), 7.55 (1H, dd, J=1.8, 5.1 Hz).

2-Acetyl-4-chloropyridine: To a solution of 4-chloro-2-pyridinecarbonitrile (5.35 g, 34.6 mmol) in benzene (50 ml) and ether (50 ml) cooled to 0° C. was added dropwise over 20 min a 2 M solution of MeMgI in ether (23 ml, 46.3 mmol). After 0.5 h, the mixture was allowed to warm to ambient temperature, and stirring continued for 2 h. The mixture was cooled to 0° C. and 2M aqueous HCl (100 ml) added. The mixture was made basic with saturated aqueous sodium bicarbonate (80 ml) and the organic layer separated and dried (MgSO4). After removal of solvent, the residue was purified by flash chromatography eluting with ethyl acetate/hexane (1:5) to afford 3.60 g (60%) of 2-acetyl-4'-chloropyiidine.

$^1$H-NMR (DMSO-d$_6$)δ 8.59 (1H, d, J=5.1 Hz), 8.04 (1H, d, J=1.8 Hz), 7.47 (1H, dd, J=1.8, 5.1 Hz), 2.72 (3 H, s).

2-(Bromoacetyl)4-chloropyridine hydrobromide: 2-(Bromoacetyl)-4-chloropyridine hydrobromide was prepared from 2-acetyl-4-chloropyridine according to the method of H. McKennis, Jr., L. B. Tunbull, E. R. Bowman, and E. Tamaki (in *J. Org. Chem.*, 1963,28,383–387S).

$^1$H-NMR (DMSO-d$_6$)δ 8.74 (1H, d, J=5.5 Hz), 8.05 (1H, d, J=1.8 Hz), 7.88 (1H, dd, J=2.2, 5.5 Hz), 5.02 (2H, s)

Step 2. 3-Amino-6-chloro-2-[(4-chloro-2-pyridinyl)carbonyl-]-1H-indole

The title compound was prepared according to the procedure described in step 2 of Example 3 from ethyl 3-amino-6-chloro-2-[(4-chloro-2-pyridinyl)carbonyl]-1 H-indole-1-carboxylate (step 1).

mp 234–235° C.

$^1$NMR (DMSO-d$_6$)δ 10.94 (1H, br s), 8.78 (1H, d, J=5.5 Hz), 8.14 (1H, d, J=2.2 Hz), 7.92 (1H, d, J=8.4 Hz), 7.80 (1H, dd, J=1.5, 5.1Hz), 7.51 (1H, d, J=1.8 Hz), 6.93 (1H, dd, J=1.8, 8.8 Hz).

Step 3. N'-[6-Chloro-2-[(4-chloro-2-pyridinyl)carbonyl]-1H-indol-3-yl]-N-methoxy-N-methylurea The title compound was prepared according to the procedure described in step 3 of Example 29 from 3-amino-6-chloro-2-[(4-chloro-2-pyridinyl)carbonyl]-1H-indole (step 2).

mp 228–229 °0 C.

IR (KBr) v 3317, 1697, 1605, 1578, 1545, 1493, 1348, 1313, 1236, 775, 742 cm$^1$ $^1$H-NMR (CDCl$_3$)δ 11.61 (1H, br s), 11.32 (1H, br s), 8.68 (1H, d, J=4.9 Hz), 8.59 (1 H, d, J=8.9 Hz), 8.40 (1H, d, J=1.8 Hz), 7.55 (1H, dd, J=2.1 and 5.3 Hz), 7.38 (1H, d, J=1.6 Hz), 7.04 (1H, dd, J=2.0 and 9.1 Hz), 3.96 (3H, s), 3.29 (3 H, s).

Example 31

N'-[6-Chloro-2-(3-Chlorobenzoyl)-1H-Indol-3-Yl]-N-Methoxy-N-Methylurea

The title compound was prepared according to the procedure described in step 3 of Example 29 from 3-amino-6-chloro-2-(3-chlorobenzoyl)-1H-indole (Example 4, step 2).

mp 167–169° C.

IR (KBr) v 3231, 1668, 1616, 1576, 1541, 1485, 1348, 1312, 1240, 920, 748 cm$^{-1}$ $^1$H-NMR (CDCl$_3$)δ 10.35 (1H, br s), 8.37 (1H, d, J=8.9 Hz), 8.19 (1H, br s), 7.78 (1 H, br s), 7.68 (1H, br d, J=7.6 Hz), 7.58(1H, br d, J=8.7 Hz), 7.49 (1H, dd, J=7.6 and 7.9 Hz), 7.29 (1H, d, J=1.3 Hz), 7.09 (1H, dd, J=1.8 and 8.9 Hz), 3.86 (3 H, s), 3.23 (3 H, s).

Example 32

N'-[6-Chloro-2-[(4-Methoxy-2-Pyridinyl)Carbonyl]-1H-Indol-3-Yl]-N-Methoxy-N-Methylurea Step 1. Ethyl 3-amino6chloro-2-[(4-methoxy-2-pyridinyl)carbonyl]-1H-indole-1-carboxylate The title compound was prepared according to the procedure described in step 2 of Example 1 from 4-chloro-2-[(ethoxycarbonyl)amino]benzonitrile (Example 1, step 1) and 2-(Bromoacetyl)methoxypyridine hydrobromide*.

$^1$H-NMR (CDCl$_3$)δ 8.42 (1H, d, J=5.9 Hz), 8.22 (1H, d, J=1.8 Hz), 7.61 (1H, d, J=2.9 Hz), 7.51 (1H, d, J=8.4 Hz), 7.27-7.23 (1H, m), 6.89 (1H, dd, J=2.6, 5.9 Hz), 5.96 (2H, br s), 3.95 (3H, s), 3.84 (2H, q, J=7.0 Hz), 0.95 (3H, t, J=7.0 Hz).

* 2-(Bromoacetyl)4-methoxyridine hydrobromide was prepared as follows;

4-Methoxy-2-pyridinecarbonitrile: The title compound was prepared from 4-methoxypiridine-N-oxide by using the procedure described for the preparation of 4-chloro-2-pyridinecarbonitrile.

$^1$H-NMR (CDCl13)δ 8.51 (1H, d, J=5.9 Hz), 7.22 (1H, d, J=2.6 Hz), 7.01 (1H, dd, 5 J=2.5, 5.9 Hz), 3.91 (3H, s).

2-Acetyl-4-methoxypyridine: The title compound was prepared from 4-methoxy-2-piridinecarbonitrile by using the procedure described for the preparation of 2-acetyl4-chloropyridine.

$^1$H-NMR (CDCl$_3$)δ 8.49 (1H, d, J=5.5 Hz), 7.58 (1H, d, J=2.6 Hz), 6.98 (1H, dd, J=2.6, 5.5 Hz), 3.91 (3H, s), 2.72 (3 H, s).

2-(Bromoacetyl)-4-methoxypyridine hydrobromide: The title compound was prepared from 2-acetylmethoxypyridine according to the method of H. McKennis, Jr., L. B. Turnbull, E. R Bowman, and E. Tamaki (in *J. Org. Chem.*, 1963, 28, 383–387S).

$^1$H-NMR (DMSO-d$_6$)δ 8.61 (1H,d, J=5.9 Hz), 7.66 (1H, d, J=2.6 Hz), 7.37 (1H, dd, J=2.6, 5.9 Hz), 5.03 (2H, s), 3.97 (3H, s).

Step 2, N'-[6Chloro-2-[(4-methoxy-2-pyridinyl)carbonyl]-1H-indol-3-yl]-N-methoxy-N-methylurea The title compound was prepared according to the procedure described in Example 15 from ethyl 3-amino6-chloro1-ethoxycarbonyl-2-[(4-methoxy-2-pyridinyl)carbonyl)-1H-indole-1-carboxylate (step 1) and N,O-dimetbylhydroxylamine hydrochloride.

mp 184–185° C.

IR (KBr) v 3258, 1680, 1589, 1566, 1537, 1481, 1352, 1308, 1217, 1157, 1126, 1024 cm$^{-1}$ $^1$H-NMR (CDCl$_3$)δ 12.01 (1H, br s), 11.29 (1H, br s), 8.54–8.57 (2H, m), 7.90 (1H, d, J=2.6 Hz), 7.38 (1H, d, J=1.8 Hz), 7.00–7.05 (2H, m), 3.97 (3H, s), 3.96 (3H, s), 3.29 (3H, s).

Example 33

N-(2-Benzoyl-6-Chloro-1H-Indol-3-Yl)Methanesulfonamide

To a solution of ethyl 3-amino-2-benzoyl-6-chloro-1H-indole-1-carboxylate (step 2 of Example 1, 200 mg, 0.58 mmol) in pyridine (5 ml) was added methanesufonyl chloride (0.07 ml, 0.87 mmol). After stirring for 72 h, the mixture was poured into water (100 ml) and extracted with diethyl ether (100 ml). The organic extract was washed consecutively with 10% aqueous citric acid (50 ml), water (50 ml), saturated aqueous sodium bicarbonate (50 ml), water (50 ml) and brine (50 ml), and dried (MgSO$_4$). After removal of solvent the residue (287 mg) was dissolved in DMF (5 ml) and LiI (362 mg, 2.7 mmol) was added. The mixture was heated at 120° C. for 5 h, cooled and partitioned between water (100 ml) and diethyl ether (100 ml). The organic layer was separated and washed with water (100 ml), brine (100 ml) and dried (MgSO$_4$). After removal of solvent the residue was purified by flash chromatography eluting with ethyl acetate/hexane (1:4) to afford the title compound (59 mg, 29%) as a yellow powder.

mp 215–218° C.

IR (KBr) v 1640,1520,1340,1150 cm$^{-1}$ $^1$H-NMR (CDCl$_3$)δ 11 .13 (1H,s), 8.91 (1H, s), 7.99 (1H, d, J 8.8 Hz), 7.94–7.84 (2H, m), 7.72–7.52 (3H, m), 7.48 (1H, d, J =1.8 Hz), 7.12 (1H, dd, J=1.5, 8.8 Hz), 2.87 (3H, s)

Example 34

N-(2-Benzoyl-6-Chloro-1H-Indol-3-Yl)Propanesulfonamide

The title compound was prepared according to the procedure described in Example 33 from ethyl 3-amino2-benzoyl-6-chloro-1H-indole-1-carboxylate (Example 1, step 2) and 1 -propanesulfonyl chloride.

mp 164–167° C.

IR (KBr) v 1620,1510, 1340,1320,1240,1145 cm$^{-1}$ $^1$H-NMR (CDCl3)δ 8.94 (1H, br s), 8.31 (1H, br s), 8.20 (1H, d, J=8.8 Hz), 7.88–7.76 (2H, m), 7.73–7.52 (3H, m), 7.35 (1H, d, J=1.8 Hz), 7.18(1H, dd, J=8.8, 1.8 Hz), 3.10–2.98 (2H, m), 1.90–1.72 (2H, m), 0.94 (3H, t, J=7.7 Hz)

Example 35

N-(2-Benzoyl-6-Chloro-1H-Indol-3-Yl)4-Methylbenzenesulfonamide

The title compound was prepared according to the procedure described in Example 33 from ethyl 3-amino-2-benzoyl-6-chloro-1H-indole-1-carboxylate (Example 1, step 2) and p-toluenesulfonyl chloride.

mp 223–225° C.

¹H-NMR (CDCl₃) δ 8.68 (1H, s), 8.18 (1H, d, J=8.4 Hz), 8.09 (1H, br s), 7.68–7.38 (7 H, m), 7.28 (1H, d, J=1.8 Hz), 7.21 (1H, dd, J=8.4, 1.8 Hz), 7.00 (2H, d, J=8.4 Hz), 2.19 (3H, s)

IR (KBr) ν 1640, 1600, 1520, 1340, 1320, 1240, 1160, 1090 cm⁻¹

Example 36

N-[6-Chloro-2-(3-Methylbenzoyl)-1H-Indol-3-Yl] Methanesulfonamide

The title compound was prepared according to the procedure described in Example 33 from ethyl 3-amino-6-chloro-2-(3-methylbenzoyl)-1H-indole-1-carboxylate (step 1 of Example 3) and methanesulfonyl chloride.

mp 164–166° C.

¹H-NMR (CDCl₃) δ 8.66 (1H, br s), 8.40 (1H, br s), 8.11 (1H, d, J=8.8 Hz), 7.65–7.58 (2H, m), 7.52–7.47 (2H, m), 7.36 (1H, d, J=1.1Hz), 7.19 (1H, dd, J=8.8, 1.8 Hz), 2.94 (3H, s), 2.48 (3H, s)

Example 37

N-[6-Chloro-2-(3-Nitrobenzoyl)-1H-Indol-3-Yl] Methanesulfonamide

Step 1. Ethyl 3-amino-6-chloro-2-(3-nitrobenzyl)-1H-indole-1-carboxylate

The title compound was prepared according to the procedure described in step 2 of Example I from 4-chloro-2-[(ethoxycarbonyl)amino]benzonitrile (Example 1, step 1) and 2-bromo-3'-nitroacetophenone.

¹H-NMR (CDCl₃) δ 8.62–8.54 (1H, m), 8.38–8.28 (1H, m), 8.21 (1H, d, J=1.8 Hz), 8.04 (1H, d, J=7.7 Hz), 7.63 (1H, dd, J=1.8, 8.1Hz), 7.57 (1H, d, J=8.4 Hz), 7.33 (1H, dd, J=1.8, 8.1Hz), 6.03 (2H, br s), 3.88 (2H, q, J=7.0 Hz), 0.94 (3H, t, J=7.0 Hz)

Step 2. N-[6-Chloro-2-(3-nitrobenzoyl)-1H-indol-3-yl]methanesulfonamide

The title compound was prepared according to the procedure described in Example 33 from ethyl 3-amino6-chloro-2-(3-nitrobenzoyl)-1H-indole-1-carboxylate (step 1) and methanesulfonyl chloride.

mp 209–212° C.

¹H-NMR (DMSO-d₆) δ 9.64 (1H, br s), 8.52–8.46 (2H, m), 8.20 (1H, d, J=7.7 Hz), 7.88–7.78 (2H, m), 7.52(11H, d, J=1.8 Hz), 7.22 (1H, dd, J=8.4, 1.8 Hz), 2.69 (3H, s)

Example 38

N-[6-Chloro-2-(3-Chlorobenzoyl)-1H-Indol-3-Yl] Methanesulfonamide

Step 1. Ethyl 3-[bis(methylsulfonyl)amino]-6-chloro-2-(3-chlorobenzoyl)-1H-indole-1-carboxylate To a solution of ethyl 3-amino-6-chloro-2-(3-chlorobenzoyl)-]-1H-indole-1-carboxylate (step 1 of Example 4, 507 mg, 1.25 mmol) in dichloromethane (15 ml) was added pyridine (0.32 ml, 4.04 mmol) and methanesulfonyl chloride (0.16 ml, 2.02 mmol). After stirring for 19 h, additional pyridine (1.3 ml, 16.2 mmol) and methanesulfonyl chloride (0.32 ml, 4.04 mmol) were added and the mixture heated at reflux for 17 h and then cooled to room temperature. The mixture was concentrated, and partitioned between ethyl acetate (200 ml) and 2 M aqueous HCl (100 ml). The organic layer was separated and washed with 2 M aqueous HCl (100 ml×2), saturated aqueous sodium bicarbonate (100 ml×3), and dried (Na₂SO₄). After removal of solvent the residue was purified by flash chromatography eluting with ethyl acetate/hexane (1:4) to afford the title compound (532 mg, 74%) as an oil.

¹H-NMR (CDCl₃) δ 8.30 (1H, d, J=1.5 Hz), 7.80 (1H, br s), 7.62–7.26 (5 H, m), 4.14 (2H, q, J=7.0 Hz), 3.51 (6 H, s), 1.07 (3H, t, J=7.0 Hz)

Step 2. N-[6-Chloro-2-(3-chlorobenzoyl)-1H-indol-3-yl]methanesulfonamide

To a solution of the ethyl 3-[bis(methylsulfonyl)amino]-6-chloro-2-(3-chlorobenzoyl)-1H-indole-1-carboxylate (step 1, 532 mg, 0.998 mmol) in ethanol (15 ml) was added a solution of potassium hydroxide (395 mg, 5.99 mmol) in water (8 ml) at room temperature. After stirring for 1 h at ambient temperature, the mixture was concentrated to ca. 10 ml, and partioned between with ethyl acetate (150 ml) and water (100 ml). The organic layer was separated and washed with water (100 ml), and dried (Na₂SO₄). Removal of the solvent by evaporation gave an crystalline residue, which was crystallized from ethanol/hexane to afford 182 mg (48%) of the title compound.

mp 196–197° C.

¹H-NMR (CDCl₃) δ 8.68 (1H, br s), 8.35 (1H, s), 8.13 (1H, d, J=9.2 Hz), 7.82–7.51 (4 H,m),7.39(1H, d, J=1.8 Hz),7.21 (1H, dd, J=1.8, 9.2 Hz),2.98(3H,s)

Example 39

N-[2-(3-Bromobenzoyl-6-Chloro-1H-Indol-3-Yl) Methanesulfonamide

Step 1. Ethyl 3-amino-2-(3-bromobenzoyl)-6-chloro-1H-indole-1-carboxylate

The title compound was prepared according to the procedure described in step 2 of Example 1 from 4chloro-2-[(ethoxycarbonyl)amino]benzonitrile (Example 1, step 1) and 2-bromo-3'-bromoacetophenone.

¹H-NMR (CDCl₃) δ 8.25 (1H, d, J=1.5 Hz), 7.90 (1H, t, J=1.8 Hz), 7.64–7.59 (2H, m), 7.54 (1H, d, J=8.4 Hz), 7.34–7.26 (2H, m), 5.87 (2H, br s). 3.84 (2H, q, J=7.0 Hz), 0.89 (3H, t, J=7.0 Hz)

Step 2. N-[2-(3-Bromobenzoyl)-6chloro-1H-indol-3-yl]methanesulfonamide

The title compound was prepared according to the procedure described in Example 38 from ethyl 3-amino-2-(3-bromobenzoyl)-6-chloro-1H-indole-1-carboxylate (step 1) and methanesulfonyl chloride.

mp 184–185° C.

¹H-NMR (CDCl₃+2 drops of DMSO-d₆) δ 11.26 (1H, br s), 9.02 (1H, br s), 8.00 (1 H, t, J=1.6 Hz), 7.96(1H, d, J=8.8 Hz), 7.83(1H, dt, J=1.3, 1.3, 7.7 Hz), 7.75 (1H, ddd, J=1.1, 1.8, 8.1Hz), 7.48 (1H, d, J=1.8 Hz), 7.44 (1H, dd, J=7.7, 8.1Hz), 7.12 (1H, dd, J=1.8, 9.2 Hz), 2.86 (3H, s).

Example 40

N-(2-Benzoyl-6-Fluoro-1H-Indol-3-Yl) Methanesulfonamide

Step 1. 2-[(Ethoxycarbonyl)amino] fluorobenzonitrile

The title compound was prepared according to the procedure described in step 1 of Example 1 (Method B) from 2-amino4-fluorobenzonitrile.

tlc: Rf=0.7 (25% ethyl acetate in hexanes)

Step 2. Ethyl 3-amino-2-benzoyl-6-fluoro-1H-indole-l-carboxylate

The title compound was prepared according to the procedure described in step 2 of Example 1 from 2-[(ethoxycarbonyl)amino]-4fluorobenzonitrile (step 1) and 2-bromoacetophenone.

$^1$H-NMR (CDCl$_3$)δ 7.94 (1H, dd, J=2.7, 10.3 Hz), 7.76–7.72 (2H, m), 7.57 (1H, dd, J =5.5, 8.8 Hz), 7.51–7.39 (3H, m), 7.06 (1H, ddd, J=2.7, 8.8, 10.3 Hz), 5.87 (2H, br s), 3.74 (2H, q, J =7.3 Hz), 0,84 (3H, t, J =7.3 Hz)

Step 3. N-(2-Benzoyl-6-fluoro-1H-indol-3-yl)methanesulfonamide

The title compound was prepared according to the procedure described in Example 38 from ethyl 3-amino-2-benzoyl-6-fluoro-1H-indole-1-carboxylate (step 2) and methanesulfonyl chloride.

mp 166–168° C.

IR (KBr) v 3350, 3250, 1740, 1630, 1505, 1450, 1335, 1260, 1140, 960, 860 cm$^{-1}$ $^1$H-NMR (CDCl$_3$)δ 8.76 (1H, br s), 8.39 (1H, br s), 8.18 (1H, dd, J=5.4, 10.1 Hz), 7.86–7.82 (2H, m), 7.69–7.58 (3H, m), 7.05–6.98 (2H, m), 2.97 (3H, s)

EXAMPLE 41

N-[5-Chloro-2-(3-Chlorobenzoyl)-1H-Indol-3-Yl] Methanesulfonamide

Step 1. Ethyl 3-amino-5-chloro-2-(3-chlorobenzoyl)-1H-indole-1-carboxylate

The title compound was prepared according to the procedure described in step 2 of Example 1 from 5-chloro-2-[(ethoxycarbonyl)amino]benzonitrile (K. O. Geolotte et al, *J. Heterocyclic Chem.*, 1990, 27, 1549) and 2-bromo-3'-chloroacetophenone (M. Kihara et al., *Tetrahedron*, 1992, 48, 67–78).

$^1$H-NMR (CDCl$_3$)δ 8.15 (1H, dd, J=10, 1Hz), 7.75 (1H, t, J=1.5 Hz), 7.60–7.43 (4H, m 7.36 (1H, t, J=8 Hz), 5.78 (2H, br s), 3.83 (2H, q, J=7 Hz), 0.92 (3H, t, J=7 Hz)

Step 2. N-[5-Chloro-2-(3-chlorobenzoyl)-1H-indol-3-yl]methanesulfonamide

The title compound was prepared according to the procedure described in Example 38 from 3-amino-5-chloro-2-(3-chlorobenzoyl)-1-ethoxycarbonyl-1H-indole (step 1) and methanesulfonyl chloride.

mp 220.5–221.2° C.

IR (KBr) v 3340, 1640, 1520, 760, 730 cm$^{-1}$ $^1$H-NMR (CDCl$_3$+2 drops of DMSO-d$_6$)δ 11.15 (1H, br s), 8.89 (1H, s), 8.02 (1H, s), 7.86 (1H, s),7.78 (1H, d, J=8 Hz), 7.60 (1 H, d, J=8 Hz), 7.53 (1H, t, J=8 Hz), 7.41(1H, d, J=8 Hz),7.33(1H, d, J=8 Hz),2.86(3H,s)

The chemical structures of the compounds prepared in the Examples 1 to 41 are summarized in the following tables.

TABLE

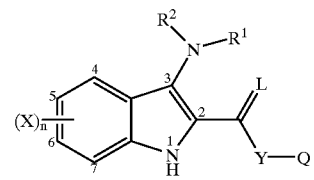

| Ex. # | (X)$_n$ | R$^1$ | R$^2$ | L | Y | Q |
|---|---|---|---|---|---|---|
| 1 | 6-Cl | H | —C(O)OCH$_3$ | O | — | phenyl |
| 2 | 6-Cl | H | —C(O)OC$_2$H$_5$ | O | — | phenyl |
| 3 | 6-Cl | H | —C(O)OC$_2$H$_5$ | O | — | 3-methylphenyl |
| 4 | 6-Cl | H | —C(O)OC$_2$H$_5$ | O | — | 3-chlorophenyl |
| 5 | 6-Cl | H | —C(O)NH$_2$ | O | — | phenyl |
| 6 | 6-Cl | H | —C(O)NH$_2$ | O | — | 3-methylphenyl |
| 7 | 6-Cl | H | —C(O)NH—C$_2$H$_5$ | O | — | phenyl |
| 8 | 6-Cl | H | —C(O)NH—CH$_3$ | O | — | phenyl |
| 9 | 6-Cl | H | —C(O)NH—C$_3$H$_7$ | O | — | phenyl |
| 10 | 6-Cl | H | —C(O)NH-isobutyl | O | — | phenyl |
| 11 | 6-Cl | H | —C(O)NH—C$_2$H$_5$OCH$_3$ | O | — | phenyl |
| 12 | 6-Cl | H | —C(O)-4-morpholine | O | — | phenyl |
| 13 | 6-Cl | H | —C(O)—N(CH$_3$)$_2$ | O | — | 3-chlorophenyl |
| 14 | 6-Cl | H | —C(O)—N(CH$_3$)(OH) | O | — | 3-chlorophenyl |
| 15 | 6-Cl | H | —C(O)—NH—CH(CH$_3$)$_2$ | O | — | phenyl |
| 16 | 6-Cl | H | —C(O)—N(CH$_3$)$_2$ | O | — | phenyl |
| 17 | 6-Cl | H | —C(O)—N(C$_2$H$_5$)$_2$ | O | — | phenyl |
| 18 | 6-Cl | H | —C(O)—N(CH$_3$)C$_2$H$_5$ | O | — | phenyl |
| 19 | 6-Cl | H | —C(O)—N(CH$_3$)C$_3$H$_7$ | O | — | phenyl |
| 20 | 6-Cl | H | —C(O)—N(C$_2$H$_5$OCH$_3$)(CH$_3$) | O | — | phenyl |

TABLE-continued

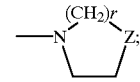

| Ex. # | (X)$_n$ | R$^1$ | R$^2$ | L | Y | Q |
|---|---|---|---|---|---|---|
| 21 | 6-Cl | H | —C(O)-4-CH$_3$-piperazine | O | — | phenyl |
| 22 | 6-Cl | H | —C(O)—N(CH$_3$)(OH) | O | — | phenyl |
| 23 | 6-Cl | H | —C(O)—N(CH$_3$)(OCH$_3$) | O | — | phenyl |
| 24 | 6-Cl | H | —C(O)—N(CH$_3$)$_2$ | O | — | 3-methylphenyl |
| 25 | 6-Cl | H | —C(O)—N(CH$_3$)(OH) | O | — | 3-methylphenyl |
| 26 | 6-Cl | H | —C(O)—N(CH$_3$)(OCH$_3$) | O | — | cyclohexyl |
| 27 | 6-Cl | H | —C(O)—N(CH$_3$)(OCH$_3$) | O | — | 3-HO-methyl-2-furyl |
| 28 | 6-Cl | H | —C(O)—N(CH$_3$)$_2$ | O | — | 3-HO-methyl-2-furyl |
| 29 | 6-Cl | H | —C(O)—N(CH$_3$)(OCH$_3$) | O | — | 4-methyl-2-pyridyl |
| 30 | 6-Cl | H | —C(O)—N(CH$_3$)(OCH$_3$) | O | — | 4-chloro-2-pyridyl |
| 31 | 6-Cl | H | —C(O)—N(CH$_3$)(OCH$_3$) | O | — | 3-chlorophenyl |
| 32 | 6-Cl | H | —C(O)—N(CH$_3$)(OCH$_3$) | O | — | 4-methoxy-2-pyridyl |
| 33 | 6-Cl | H | —S(O)$_2$—CH$_3$ | O | — | phenyl |
| 34 | 6-Cl | H | —S(O)$_2$—C$_3$H$_7$ | O | — | phenyl |
| 35 | 6-Cl | H | —S(O)$_2$-4-methylphenyl | O | — | phenyl |
| 36 | 6-Cl | H | —S(O)$_2$—CH$_3$ | O | — | 3-methylphenyl |
| 37 | 6-Cl | H | —S(O)$_2$—CH$_3$ | O | — | 3-nitrophenyl |
| 38 | 6-Cl | H | —S(O)$_2$—CH$_3$ | O | — | 3-chlorophenyl |
| 39 | 6-Cl | H | —S(O)$_2$—CH$_3$ | O | — | 3-bromophenyl |
| 40 | 6-F | H | —S(O)$_2$—CH$_3$ | O | — | phenyl |
| 41 | 5-Cl | H | —S(O)$_2$—CH$_3$ | O | — | 3-chlorophenyl |

What is claimed is:

1. A compound of the following formula:

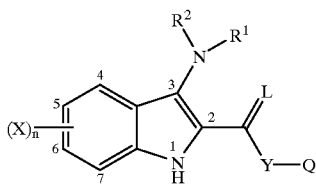

(I)

or the pharmaceutically acceptable salts thereof wherein
R$^1$ is hydrogen or C$_{1-4}$ alkyl; R$^2$ is C(=L')R$^3$ or SO$_2$R$^4$; Y is a direct bond or C$_{1-4}$ alkylene; L and L' are independently oxygen or sulfur;

Q is selected from the following:
(Q-a) C$_{1-6}$ alkyl,
(Q-b) halo-substituted C$_{1-4}$ alkyl,
(Q-c) C$_{3-7}$ cycloalkyl optionally substituted with one or two substituents independently selected from C$_{1-4}$ alkyl, halo-substituted C$_{1-4}$ alkyl, C$_{1-4}$ alkoxy, hydroxy and halo,
(Q-d) phenyl or naphthyl, the phenyl and naphthyl being optionally substituted with one, two or three substituents independently selected from halo, C$_{1-4}$ alkyl, halo-substituted C$_{1-4}$ alkyl, hydroxy, C$_{1-4}$ alkoxy, nitro, halo-substituted C$_{1-4}$ alkoxy, S(O)$_m$R$^5$, SO$_2$NH$_2$, SO$_2$N(C$_{1-4}$ alkyl)$_2$, amino, C$_{1-4}$ alkylamino, di-(C$_{1-4}$ alkyl)amino, NR$^1$C(O)R$^5$, CN, C$_{1-4}$ alkyl-OH and C$_{1-4}$ alkyl-OR$^5$,
(Q-e) a 5-membered monocyclic aromatic group containing one heteroatom selected from O, S and N and optionally containing one, two or three nitrogen atom(s) in addition to said heteroatom, and said monocyclic aromatic group being optionally substituted with one, two or three substituents independently selected from halo, C$_{1-4}$ alkyl, halo-substituted C$_{1-4}$ alkyl, hydroxy, C$_{1-4}$ alkoxy, halo-substituted C$_{1-4}$ alkoxy, amino, C$_{1-4}$ alkylamino, di-(C$_{1-4}$ alkyl)amino, C$_{1-4}$ alkyl-OH and C$_{1-4}$ alkyl-OR$^5$, and
(Q-f) a 6-membered monocyclic aromatic group containing one nitrogen atom and optionally containing one, two or three additional nitrogen atom(s), and said monocyclic armomatic group being optionally substituted with one, two or three substituents independently selected from halo, C$_{1-4}$ alkyl, halo-substituted C$_{1-4}$ alkyl, hydroxy, C$_{1-4}$ alkoxy, halo-substituted C$_{1-4}$ alkoxy, amino, C$_{1-4}$ alkylamino, di-(C$_{1-4}$ alkyl)amino, C$_{1-4}$ alkyl-OH and C$_{1-4}$ alkyl-OR$^5$;

R$^3$ is —OR$^6$, —NR$^7$R$^8$, N(OR$^1$)R$^7$ or a group of formula:

$$-N\underbrace{(CH_2)_r}Z;$$

Z is a direct bond, oxygen, sulfur or NR$^5$;
R$^4$ is C$_{1-6}$ alkyl, halo-substituted C$_{1-4}$ alkyl, C$_{1-4}$ alkyl-OH, —NR$^7$R$^8$, phenyl or naphthyl, the phenyl and naphthyl being optionally substituted with one, two or three substituents independently selected from halo, C$_{1-4}$ alkyl, halo-substituted C$_{1-4}$ alkyl, hydroxy, C$_{1-4}$ alkoxy and halo-substituted C$_{1-4}$ alkoxy;
R$^5$ is C$_{1-4}$ alkyl or halo-substituted C$_{1-4}$ alkyl;
R$^6$ is C$_{1-4}$ alkyl, C$_{3-7}$ cycloalkyl, C$_{1-4}$ alkyl-C$_{3-7}$ cycloalkyl, halo-substituted C$_{1-4}$ alkyl, C$_{1-4}$ alkyl-phenyl or phenyl, the phenyl moiety being optionally substituted with one, or two substituents independently selected from halo, $C_{1-4}$ alkyl, halo-substituted $C_{1-4}$ alkyl, hydroxy, $C_{1-4}$ alkoxy, $C_{1-4}$ alkylthio, amino, di-($C_{1-4}$ alkyl)amino and nitro;

$R^7$ and $R^8$ are independently selected from the following:
(a) hydrogen,
(b) $C_{1-6}$ alkyl optionally substituted with a substituent independently selected from halo, hydroxy, $C_{1-4}$ alkoxy, amino, $C_{1-4}$ alkylamino and di-($C_{1-4}$ alkyl)amino,
(c) $C_{3-7}$ cycloalkyl optionally substituted with a substituent independently selected from hydroxy, $C_{1-4}$ alkyl and $C_{1-4}$ alkoxy,
(d) $C_{1-4}$ alkyl-$C_{3-7}$ cycloalkyl optionally substituted with a substituent independently selected from hydroxy, $C_{1-4}$ alkyl and $C_{1-4}$ alkoxy, and
(f) $C_{1-4}$ alkyl-phenyl or phenyl, the phenyl moiety being optionally substituted with one or two substituents independently selected from halo, $C_{1-4}$ alkyl, halo-substituted $C_{1-4}$ alkyl, hydroxy, $C_{1-4}$ alkoxy, $C_{1-4}$ alkylthio, nitro, amino, di-($C_{1-4}$ alkyl)amino and CN;

X is independently selected from halo, $C_{1-4}$ alkyl, halo-substituted $C_{1-4}$ alkyl, hydroxy, $C_{1-4}$ alkoxy, halo-substituted $C_{1-4}$ alkoxy, $C_{1-4}$ alkylthio, nitro, amino, di-($C_{1-4}$ alkyl)amino and CN;

m is 0, 1 or 2; n is 0, 1, 2 or 3; and r is 1, 2 or 3.

2. A compound according to claim 1, wherein $R^1$ is hydrogen, methyl, ethyl, propyl or butyl; $R^2$ is $C(=L')R^3$ or $SO_2R^4$; Y is a direct bond, methylene, ethylene, trimethyle or tetramethylene; L and L' are oxygen;

Q is selected from the following:
(Q-c) $C_{3-7}$ cycloalkyl optionally substituted with one or two substituents independently selected from $C_{1-4}$ alkyl, halo-substituted $C_{1-4}$ alkyl, $C_{1-4}$ alkoxy, hydroxy and halo,
(Q-d) phenyl or naphthyl, the phenyl and naphthyl being optionally substituted with one, two or three substituents independently selected from halo, $C_{1-4}$ alkyl, halo-substituted $C_{1-4}$ alkyl, hydroxy, $C_{1-4}$ alkoxy, nitro, halo-substituted $C_{1-4}$ alkoxy, $S(O)_mR^5$, $SO_2NH_2$, $SO_2N(C_{1-4}$ alkyl$)_2$, amino, $C_{1-4}$ alkylamino, di-($C_{1-4}$ alkyl)amino, $NR^1C(O)R^5$, CN, $C_{1-4}$ alkyl-OH and $C_{1-4}$ alkyl-$OR^5$,
(Q-e) a 5-membered monocyclic aromatic group selected from thienyl, furyl, thiazolyl, imidazolyl, pyrrolyl, oxazolyl, pyrazolyl, tetrazolyl, triazolyl, oxadiazolyl and thiadiazolyl, and said monocyclic armomatic group being optionally substituted with one, two or three substituents independently selected from halo, $C_{1-4}$ alkyl, halo-substituted $C_{1-4}$ alkyl, hydroxy, $C_{1-4}$ alkoxy, halo-substituted $C_{1-4}$ alkoxy, amino, $C_{1-4}$ alkylamino, di-($C_{1-4}$ alkyl)amino, $C_{1-4}$ alkyl-$OR^5$, and
(Q-f) a 6-membered monocyclic aromatic group selected from pyridyl, pyrazinyl, pyrimidinyl, pyridazinyl, triazinyl and tetrazinyl, and said monocyclic armomatic group being optionally substituted with one, two or three substituents independently selected from halo, $C_{1-4}$ alkyl, halo-substituted $C_{1-4}$ alkyl, hydroxy, $C_{1-4}$ alkoxy, halo-substituted $C_{1-4}$ alkoxy, amino, $C_{1-4}$ alkylamino, di-($C_{1-4}$ alkyl)amino, $C_{1-4}$ alkyl-OH and $C_{1-4}$ alkyl-$OR^5$;

$R^3$ is $-OR^6$, $-NR^7R^8$, $N(OR^1)R^7$ or a group of formula:

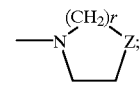

Z is a direct bond, oxygen or $NR^5$;

$R^4$ is $C_{1-6}$ alkyl, halo-substituted $C_{1-4}$ alkyl, $C_{1-4}$ alkyl-OH, $-NR^7R^8$ or phenyl optionally substituted with one or two substituents independently selected from halo, $C_{1-4}$ alkyl, halo-substituted $C_{1-4}$ alkyl, hydroxy, $C_{1-4}$ alkoxy and halo-substituted $C_{1-4}$ alkoxy;

$R^5$ is $C_{1-4}$ alkyl or $CF_3$;

$R^6$ is $C_{1-4}$ alkyl, $C_{3-7}$ cycloalkyl or halo-substituted $C_{1-4}$ alkyl;

$R^7$ and $R^8$ are independently selected from the following:
(a) hydrogen,
(b) $C_{1-6}$ alkyl optionally substituted with a substituent independently selected from halo, hydroxy, $C_{1-4}$ alkoxy, amino, $C_{1-4}$ alkylamino and di-($C_{1-4}$ alkyl)amino,
(C) $C_{3-7}$ cycloalkyl optionally substituted with a substituent independently selected from hydroxy, $C_{1-4}$ alkyl and $C_{1-4}$ alkoxy, X is independently selected from halo, $C_{1-4}$ alkyl, halo-substituted $C_{1-4}$ alkyl, $C_{1-4}$ alkoxy, hydroxy, nitro and CN;

m is 0, 1 or 2; n is 0, 1 or 2; and r is 1, 2 or 3.

3. A compound according to claim 2, wherein $R^1$ is hydrogen, methyl or ethyl; $R^2$ is $C(=O)R^3$ or $SO_2R^4$; Y is a direct bond or methylene;

Q is selected from the following:
(Q-c) $C_{3-7}$ cycloalkyl optionally substituted with methyl, ethyl or hydroxy,
(Q-d) phenyl optionally substituted with one or two substituents independently selected from halo, $C_{1-4}$ alkyl, halo-substituted $C_{1-4}$ alkyl, hydroxy, $C_{1-4}$ alkoxy, halo-substituted $C_{1-4}$ alkoxy, nitro and amino,
(Q-e) a 5-membered monocyclic aromatic group selected from thienyl, furyl, thiazolyl, imidazolyl, pyrrolyl, oxazolyl, pyrazolyl, tetrazolyl and triazolyl, and said monocyclic armomatic group being optionally substituted with one or two substituents independently selected from F, Cl, Br, methyl, ethyl, propyl, $CF_3$, hydroxy, methoxy, ethoxy, $CF_3O-$, amino, methylamino, dimethylamino, hydroxymethyl, hydroxyethyl, hydroxypropyl, hydroxybutyl, methoxylmethyl, methoxyethyl and ethoxymethyl, and
(Q-f) a 6-membered monocyclic aromatic group selected from pyridyl, pyrazinyl, pyrimidinyl and pyridazinyl, and said monocyclic armomatic group being optionally substituted with one or two substituents independently selected from F, Cl, Br, methyl, ethyl, propyl, $CF_3$, hydroxy, methoxy, ethoxy, $CF_3O-$, amino, methylamino, dimethylamino, hydroxymethyl, hydroxyethyl, hydroxypropyl, hydroxybutyl, methoxylmethyl, methoxyethyl and ethoxymethyl;

$R^3$ is —$OR^6$, —$NR^7R^8$, $N(OR^1)R^7$ or a group of formula:

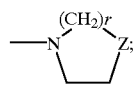

Z is oxygen or $NR^5$;
$R^4$ is methyl, ethyl, propyl, butyl, $CF_3$, hydroxymethyl, hydroxyethyl, hydroxypropyl, hydroxybutyl, amino, methylamino, dimethylamino or phenyl optionally substituted with F, Cl, Br, methyl, ethyl, propyl, $CF_3$, hydroxy, methoxy, ethoxy or $CF_3O$—;
$R^5$ is methyl, ethyl or propyl;
$R^6$ is methyl, ethyl, propyl, butyl, cyclobutyl, cyclopentyl, cyclohexyl or $CF_3$;
$R^7$ and $R^8$ are independently selected from the following:
(a) hydrogen,
(b) methyl, ethyl, propyl, butyl, pentyl, methoxyethyl, methoxymethyl, ethoxymethyl or methoxymethyl,
X is F, Cl, Br, methyl, ethyl, isopropyl, $CF_3$, methoxy, nitro or CN;
n is 0 or 1; and r is 2.

4. A compound according to claim 3, wherein
$R^1$ is hydrogen or methyl; $R^2$ is C(=O)$R^3$ or $SO_2R^4$; Y is a direct bond;
Q is selected from the following:
(Q-c) cyclobutyl, cyclopentyl, cyclohexyl, methylcyclohexyl or cycloheptyl,
(Q-d) phenyl optionally substituted with one or two substituents independently selected from F, Cl, Br, methyl, ethyl, propyl, butyl, $CF_3$, hydroxy, methoxy, $CF_3O$—, nitro and amino,
(Q-e) thienyl or furyl, and the thienyl and furyl optionally substituted with F, Cl, Br, methyl, ethyl, propyl, $CF_3$, hydroxy, methoxy, ethoxy, $CF_3O$—, amino, methylamino, dimethylamino, hydroxymethyl, hydroxyethyl, hydroxypropyl, hydroxybutyl, methoxylmethtyl, methoxyethyl or ethoxymethyl, and
(Q-f) pyridyl optionally substituted with F, Cl, Br, methyl, ethyl, propyl, $CF_3$, hydroxy, methoxy, ethoxy, $CF_3O$—, amino, methylamino, dimethylamino, hydroxymethyl, hydroxyethyl, hydroxypropyl, hydroxybutyl, methoxylmethtyl, methoxyethyl or ethoxymethyl;
$R^3$ is —$OR^6$, —$NR^7R^8$, $N(OR^1)R^7$ or a group of formula:

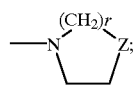

Z is oxygen or $NR^5$;
$R^4$ is methyl, ethyl or propyl, $CF_3$, hydroxyethyl, bydroxypropyl, amino or phenyl optionally substituted with F, Cl, Br, methyl, ethyl, propyl, $CF_3$, hydroxy, methoxy, ethoxy or $CF_3O$—;
$R^5$ is methyl, ethyl or propyl;
$R^6$ is methyl, ethyl, propyl, butyl, cyclobutyl, cyclopentyl, cyclohexyl or $CF_3$;
$R^7$ and $R^8$ are independently selected from the following:
(a) hydrogen,
(b) methyl, ethyl, n-propyl, isopropyl, n-butyl, isobutyl, pentyl, methoxyethyl or methoxymethyl, X is F, Cl, Br, methyl or methoxy; and n is 1.

5. A compound according to claim 4, wherein
Q is selected from the following:
(Q-c) cyclohexyl,
(Q-d) phenyl optionally substituted with F, Cl, Br, methyl, ethyl, propyl, nitro, methoxy or $CF_3$,
(Q-e) furyl optionally substituted with methyl, ethyl, propyl, hydroxymethyl, hydroxyethyl, hydroxypropyl, hydroxybutyl, methoxylmethtyl, methoxyethyl or ethoxymethyl, and
(Q-f) pyridyl optionally substituted with F, Cl, Br, methyl, ethyl, propyl, $CF_3$, hydroxy, methoxy, ethoxy or $CF_3O$—;
$R^3$ is —$OR^6$, —$NR^7R^8$, $N(OR^1)R^7$ or a group of formula:

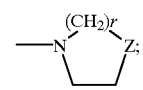

Z is oxygen or $NR^5$;
$R^4$ is methyl, ethyl, propyl or phenyl optionally substituted with methyl or ethyl;
$R^5$ is methyl or ethyl
$R^6$ is methyl, ethyl or propyl;
$R^7$ and $R^8$ are independently selected from the following:
(a) hydrogen,
(b) methyl, ethyl, n-propyl, isopropyl, n-butyl, isobutyl, pentyl, methoxyethyl or methoxymethyl,
X is F, Cl or Br; and n is 1.

6. A compound according to claim 5, wherein
Q is cyclohexyl, chlorophenyl, bromophenyl, methylphenyl, nitrophenyl, hydroxymethylfuryl, methylpyridyl, chloropyridyl or methoxypyridyl $R^3$ is methoxy, ethoxy, amino, methylamino, ethylamino, propylamino, isobutylamino, methoxylethylamino, dimethylamino, diethylamino, —N($CH_3$)$C_2H_5$, —N($CH_3$)$C_3H_7$, isopropylamino, —N(OH)$CH_3$, —N(O$CH_3$)$CH_3$, —N($CH_2CH_2OCH_3$)$CH_3$, 4morpholine or 4-methylpiperazinyl;
$R^4$ is methyl, propyl or methylphenyl; and X is F or Cl.

7. A compound according to claim 1 selected from
methyl N-(2-benzoyl-6-chloro-1H-indol-3yl)carbamate;
ethyl N-(2-benzoyl-6-chloro-1H-indol-3-yl)carbamate;
ethyl N-(6-chloro-2-(3-methylbenzoyl)-1H-indol-3-yl]carbamate;
ethyl N-[6-chloro-2-(3-chlorobenzoyl)-1H-indol-3-yl]carbamate;
N-(2-benzoyl-6-chloro-1H-indol-3-yl)urea;
N-[6-chloro-2-(3-methylbenzoyl)-1H-indol-3-yl]urea;
N-(2-benzoyl-6-chloro-1H-indol-3-yl)-N'-ethylurea;
N-(2-benzoyl-6-chloro-1H-indol-3-yl)N'-methylurea;
N-(2-benzoyl-6-chloro-1H-indol-3-yl)-N'-propylurea;
N-(2-benzoyl-6-chloro-1H-indol-3-yl)-N'-isobutylurea;
N-(2-benzoyl-6-chloro-1H-indol-3-yl)-N'-(2-methoxyethyl)urea;
N-(2-benzoyl-6-chloro-1H-indol-3-yl)4-morpholinecarboxamide;
N'-[6-chloro-2-(3-chlorobenzoyl)- 1H-indol-3-yl]-N,N-dimethylurea;
N'-[6-chloro-2-(3-chlorobenzoyl)-1H-indol-3-yl]-N-hydroxy-N-methylurea;
N-(2-benzoyl-6-chloro-1H-indol-3-yl)-N'-isopropylurea;
N'-(2-benzoyl-6-chloro-1H-indol-3-yl)-N,N-dimethylurea;
N'-(2-benzoyl-6chloro-1H-indol-3-yl)-N,N-diethylurea;
N'-(2-benzoyl-6-chloro-1H-indol-3-yl)-N-ethyl-N-methylurea;

N'-(2-benzoyl-6-chloro-1H-indol-3-yl)-N-methyl-N-propylurea;
N'-(2-benzoyl-6-chloro-1H-indol-3-yl)-N-(2-methoxyethyl)-N-methylurea;
N-(2-benzoyl-6-chloro-1H-indol-3-yl)4-methyl-1-piperazinecarboxamide;
N'-(2-benzoyl-6-chloro-1H-indol-3-yl)-N-hydroxy-N-methylurea;
N'-(2-benzoyl-6-chloro-1H-indol-3-yl)-N-methoxy-N-methylurea;
N'-[6-chloro-2-(3-methylbenzoyl)-1H-indol-3-yl]-N,N-dimethylurea;
N'-[6-chloro-2-(3-methylbenzoyl)-1H-indol-3-yl]-N-hydroxy-N-methylurea;
N'-[6-chloro-2-(cyclohexylcarbonyl)-1H-indol-3-yl]-N-methoxy-N-methylurea;
N'-[6-chloro-2-(3-hydroxymethyl-2-furoyl)-1H-indol-3-yl]-N-methoxy-N-methylurea,
N'-[6-chloro-2-(3-hydroxymethyl-2-furoyl)-1H-indol-3-yl]-N,N-dimethylurea;
N'-[6-chloro-2-[(4-methyl-2-pyridinyl carbonyl]-1H-indol-3-yl]-N-methoxy-N-methylurea;
N'-[6-chloro-2-[(4-chloro-2-pyridinyl)carbonyl]-1H-indol-3-yl]-N-methoxy-N-methylurea;
N'-[6-chloro-2-(3-chlorobenzoyl)-1H-indol-3-yl]-N-methoxy-N-methylurea;
N'-[6-chloro-2-[(4-methoxy-2-pyridinyl)carbonyl]-1H-indol-3-yl]-N-methoxy-N-methylurea;
N-(2-benzoyl-6-chloro-1H-indol-3-yl)methansulfonamide;
N-(2-benzoyl-6-chloro-1H-indol-3-yl)propansulfonamnide;
N-(2-benzoyl-6-chloro-1H-indol-3-yl)-4-methylbenzenesulfonamide);
N-[6-chloro-2-(3-methylbenzoyl)-1H-indol-3-yl]methanesulfonamide;
N-[6-chloro-2-(3-methylbenzoyl)-1H-indol-3-yl]methanesulfonamide;
N-[6-chloro-2-(3-chlorobenzoyl)-1H-indol-3-yl]methanesulfonamide;
N-[2-(3-bromobenzoyl)-6-chloro-1H-indol-3-yl]methanesulfonamide;
N-(2-benzoyl-6-fluoro-1H-indol-3-yl)methanesulfonamide; and
N-[5-chloro-2-(3-chlorobenzoyl)-1H-indol-3-yl]methanesulfonamide.

8. A compound according to claim 7 selected from
ethyl N-(2-benzoyl-6-chloro-1H-indol-3-yl)carbamate;
N-(2-benzoyl6-chloro-1H-indol-3-yl)urea;
N-[6-chloro-2-(3-methylbenzoyl)-1H-indol-3-yl]urea;
N-(2-benzoyl-6-chloro-1H-indol-3-yl)-N'-ethylurea;
N-(2-benzoyl-6-chloro-1H-indol-3-yl)N'-methylurea;
N-(2-benzoyl-6-chloro-1H-indol-3-yl)-N'-propylurea;
N-(2-benzoyl-6-chloro-1H-indol-3-yl)N'-isobutylurea;
N-(2-benzoyl-6-chloro-1H-indol-3-yl)-N'-(2-methoxyethyl)urea;
N'-[6-chloro-2-(3-chlorobenzoyl)-1H-indol-3-yl]-N,Nimethylurea;
N'-[6-chloro-2-(3-chlorobenzoyl)-1H-indol-3-yl]-N-hydroxy-N-methylurea;
N-(2-benzoyl-6-chloro-1H-indol-3-yl)-N'-isopropylurea;
N'-(2-benzoyl-6-chloro-1H-indol-3-yl)-N,N-dimethylurea;
N'-(2-benzoyl-6-chloro-1H-indol-3-yl)-N,N-diethylurea;
N'-(2-benzoyl-6-chloro-1H-indol-3-yl)-N-methyl-N-propylurea;
N'-(2-benzoyl-6-chloro-1H-indol-3-yl)-N-hydroxy-N-methylurea;
N'-(2-benzoyl-6-chloro-1H-indol-3-yl)-N-methoxy-N-methylurea;
N'-[6chloro-2- (3-methylbenzoyl)-1H-indol-3-yl]-N,N-dimethylurea;
N'-[6-chloro-2-(3-hydroxymethyl-2-furoyl)-1H-indol-3-yl]-N-methoxy-N-methylurea
N'-[6-chloro-2-[(4-methyl-2-pyridinyl)carbonyl]-1H-indol-3-yl]-N-methoxy-N-methylurea;
N'-[6-chloro-2-[(4-chloro-2-pyridinyl)carbonyl]-1H-indol-3-yl]-N-methoxy-N-methylurea;
N'-[6-chloro-2-[(4-methoxy-2-pyridinyl)carbonyl]-1H-indol-3-yl]-N-methoxy-N-methylurea;
N-(2-benzoyl-6-chloro-1H-indol-3-yl)methanesulfonamide;
N-(2-benzoyl-6-chloro-1H-indol-3-yl)propanesulfonamide;
N-[6-chloro-2-(3-methylbenzoyl)-1H-indol-3-yl]methanesulfonamide;
N-[6-chloro-2-(3-chlorobenzoyl)-1H-indol-3-yl]methanesulfonamide;
N-[2-(3-bromobenzoyl)-6-chloro-1H-indol-3-yl]methanesulfonamide;
N-(2-benzoyl-6-fluoro-1H-indol-3-yl)methanesulfonamide; and
N-[5-chloro-2-(3-chlorobenzoyl-1H-indol-3-yl]methanesulfonamide.

9. A compound according to claim 8 selected from
N-(2-benzoyl-6-chloro-1H-indol-3-yl)urea;
N-[6-chloro-2-(3-methylbenzoyl)-1H-indol-3-yl]urea;
N'-(2-benzoyl-6-chloro-1H-indol-3-yl)N-methoxy-N-methylurea;
N'-[6-chloro-2-(3-hydroxymethyl-2-furoyl)-1H-indol-3-yl]-N-methoxy-N-methylurea;
N-(2-benzoyl-6-chloro-1H-indol-3-yl)methanesulfonamide;
N-[6-chloro-2-(3-methylbenzoyl)-1H-indol-3-yl]methanesulfonamide;
N-[6-chloro-2-(3-chlorobenzoyl)-1H-indol-3-yl]methanesulfonamide; and
N-[2-(3-bromobenzoyl)-6chloro-1H-indol-3-yl]methanesulfonamide.

10. A pharmaceutical composition useful for the treatment of a medical condition selected from the group consisting of pain, fever, inflammation, low back and neck pain, headache, toothache, sprains, strains, myosistis, synovitis, arthritis, bursitis, burns, which comprises a compound according to claim I effective in such treatments, and a pharmaceutically inert carrier.

11. A method for the treatment of a medical condition selected from the group consisting of pain, fever, inflammation, low back and neck pain, headache, toothache, sprains, strains, myosistis, synovitis, arthritis, bursitis, burns, in a mammalian subject, which comprises administering to said mammal in need of such treatment an effective amount of a compound according to claim 1 or a pharmaceutically acceptable salt thereof.

* * * * *